(12) United States Patent
Hagiopol et al.

(10) Patent No.: US 9,464,193 B2
(45) Date of Patent: Oct. 11, 2016

(54) MODIFIED POLYPHENOL BINDER COMPOSITIONS AND METHODS FOR MAKING AND USING SAME

(71) Applicant: Georgia-Pacific Chemicals LLC, Atlanta, GA (US)

(72) Inventors: Cornel Hagiopol, Lilburn, GA (US); Derek L. Atkinson, Lawrenceville, GA (US)

(73) Assignee: Georgia-Pacific Chemicals LLC, Atlanta, GA (US)

( * ) Notice: Subject to any disclaimer, the term of this patent is extended or adjusted under 35 U.S.C. 154(b) by 0 days.

(21) Appl. No.: 14/880,726

(22) Filed: Oct. 12, 2015

(65) Prior Publication Data

US 2016/0032104 A1 Feb. 4, 2016

Related U.S. Application Data

(63) Continuation of application No. 14/040,796, filed on Sep. 30, 2013, now Pat. No. 9,157,016.

(60) Provisional application No. 61/708,388, filed on Oct. 1, 2012.

(51) Int. Cl.

| | | |
|---|---|---|
| *C09J 171/08* | (2006.01) | |
| *C08L 97/02* | (2006.01) | |
| *C09J 197/00* | (2006.01) | |
| *C09J 161/14* | (2006.01) | |
| *C09J 163/00* | (2006.01) | |
| *C09J 167/02* | (2006.01) | |
| *C09J 161/06* | (2006.01) | |
| *C08G 8/28* | (2006.01) | |
| *C08G 61/12* | (2006.01) | |
| *C08G 65/00* | (2006.01) | |
| *C08L 33/00* | (2006.01) | |
| *C08L 65/00* | (2006.01) | |

(52) U.S. Cl.
CPC ............ *C08L 97/02* (2013.01); *C08G 8/28* (2013.01); *C08G 61/12* (2013.01); *C08G 65/002* (2013.01); *C08L 33/00* (2013.01); *C08L 65/00* (2013.01); *C09J 161/06* (2013.01); *C09J 161/14* (2013.01); *C09J 163/00* (2013.01); *C09J 167/02* (2013.01); *C09J 171/08* (2013.01); *C09J 197/005* (2013.01)

(58) Field of Classification Search
CPC ....... C09J 171/08; C09J 161/06; C08L 97/02
USPC .......... 524/592, 604, 596; 525/472; 528/87, 528/192
See application file for complete search history.

(56) References Cited

U.S. PATENT DOCUMENTS

2007/0218307 A1 9/2007 Li
2010/0160488 A1* 6/2010 Assmann ............ C08F 283/00
523/130

FOREIGN PATENT DOCUMENTS

CN 1608159 4/2005
WO 03/042451 A2 5/2003

* cited by examiner

*Primary Examiner* — Kelechi Egwim
(74) *Attorney, Agent, or Firm* — Ram W. Sabnis

(57) ABSTRACT

Modified polyphenol binder compositions and methods for making and using same are provided. In at least one specific embodiment, the binder composition can include at least one unsaturated monomer and at least one polyphenolic compound. The polyphenolic compound can include a lignin, a tannin, a novolac resin, a modified phenol formaldehyde resin, bis-phenol A, humic acid, or any mixture thereof.

20 Claims, No Drawings

MODIFIED POLYPHENOL BINDER COMPOSITIONS AND METHODS FOR MAKING AND USING SAME

CROSS-REFERENCE TO RELATED APPLICATIONS

This application is a continuation of co-pending U.S. patent application Ser. No. 14/040,796, filed on Sep. 30, 2013, which claims priority to U.S. Provisional Patent Application No. 61/708,388, filed on Oct. 1, 2012, which are both incorporated by reference herein.

BACKGROUND

1. Field

Embodiments described herein generally relate to modified polyphenol binder compositions and methods for making and using same. More particularly, such embodiments relate to modified polyphenol binder compositions for making composite lignocellulose containing products.

2. Description of the Related Art

The production of lignocellulose containing products requires an adhesive or binder to bond the discrete, particulates, fibers, veneers, or other substrates to one another. Typical lignocellulose containing composite products include particleboard, fiberboard, plywood, and the like. Conventional binders used in the production of these products frequently contain formaldehyde based resins such as urea-formaldehyde ("UF"), melamine-formaldehyde ("MF"), and phenol-formaldehyde ("PF") binders. While these formaldehyde based resins produce finished products having desirable properties, such as strength, these binders also release formaldehyde into the environment during the production of the binder, curing of the binder/lignocellulose containing product, as well as, from the final product made using the binder.

Various techniques have been used to reduce the amount of formaldehyde released from formaldehyde based resins. For example, the addition of formaldehyde scavengers to the resin and/or various modifications to the particular synthesis steps used to make the formaldehyde based resin, such as the addition of urea as a reactant late in the binder synthesis, are often used in an attempt to reduce formaldehyde emission. These attempts to reduce formaldehyde emission, however, are accompanied with undesirable effects such as longer cure time, reduced resin shelf-life, reduced product strength, reduced tolerance for processing variations, and/or inferior moisture resistance.

There is a need, therefore, for improved binder compositions for making composite lignocellulose containing products having reduced or no formaldehyde emission.

SUMMARY

Modified polyphenol binder compositions and methods for making and using same are provided. In at least one specific embodiment, the binder composition can include at least one unsaturated monomer and at least one polyphenolic compound. The polyphenolic compound can include a lignin, a tannin, a novolac resin, a modified phenol formaldehyde resin, bis-phenol A, humic acid, or any mixture thereof.

In at least one specific embodiment, a method for preparing a composite product can include contacting a plurality of lignocellulose substrates with a binder composition. The binder composition can include at least one unsaturated monomer and at least one polyphenolic compound. The polyphenolic compound can include a lignin, a tannin, a novolac resin, a modified phenol formaldehyde resin, bis-phenol A, humic acid, or any mixture thereof. The method can also include at least partially curing the binder composition to produce a composite lignocellulose-containing product.

In at least one specific embodiment, a composite product can include a plurality of lignocellulose substrates and an at least partially cured binder composition. The binder composition, prior to at least partially curing, can include at least one unsaturated monomer and at least one polyphenolic compound. The polyphenolic compound can include a lignin, a tannin, a novolac resin, a modified phenol formaldehyde resin, bis-phenol A, humic acid, or any mixture thereof.

DETAILED DESCRIPTION

The binder composition can be or include a mixture of at least one unsaturated monomer and at least one polyphenolic compound. The binder composition can be or include a reaction product between at least one unsaturated monomer and at least one polyphenolic compound. Illustrative polyphenolic compounds can include, but are not limited to, one or more lignins, one or more tannins, one or more novolac resins, one or more modified phenol formaldehyde resins, bis-phenol A, humic acid, any mixture thereof, and/or any combination thereof. Said another way, the binder composition can be produced by combining and/or at least partially reacting the one or more unsaturated monomers with the one or more polyphenolic compounds. Any suitable unsaturated monomer or combination of unsaturated monomers can be used to produce the binder compositions discussed and described herein. Preferably the unsaturated monomers are nonionic. Illustrative unsaturated monomers can include, but are not limited to, one or more unsaturated glycidyl ethers, one or more unsaturated glycidyl esters, one or more unsaturated mono-epoxides, one or more unsaturated methylol compounds, maleic anhydride, or any combination thereof.

Illustrative unsaturated glycidyl ethers can be represented by the general Formula (I):

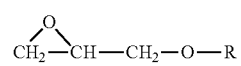

Formula (I)

where R can be an ethylenically unsaturated radical such as vinyl, allyl, alkenyl, and the like. Suitable glycidyl ethers can include, but are not limited to, vinyl glycidyl ether, isopropenyl glycidyl ether, oleyl glycidyl ether, allyl glycidyl ether, p-vinylbenzyl glycidyl ether, o-allyl phenyl glycidyl ether, butenyl glycidyl ether, 4-vinylcyclohexyl glycidyl ether, abietylglycidyl ether, cyclohexenylmethyl glycidyl ether, methallyl glycidyl ether, or any combination thereof.

Illustrative unsaturated glycidyl esters can be represented by the general Formula (II):

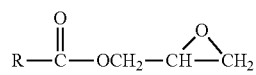

Formula (II)

where R can be an unsaturated, unsubstituted alkyl radical having from two to 19 carbon atoms. Suitable glycidyl esters can include, but are not limited to, glycidyl methacrylate, glycidyl acrylate, glycidyl crotonate, glycidyl oleate, di-glycidyl maleate, di-glycidyl fumarate, or any combination thereof.

Illustrative unsaturated mono-epoxides can include, but are not limited to, linear or cycloaliphatic epoxy compounds, where the unsaturation is terminal. Suitable unsaturated mono-epoxides can be represented by the general Formula (III):

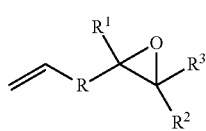

Formula (III)

where R can be a single bond or an alkylene optionally containing alkyl pendant groups; $R^1$, $R^2$, and $R^3$ can independently be hydrogen, alkyl straight, branched or cyclic, or any two of $R^1$, $R^2$, or $R^3$ can be alkylene and combined to form a 5 to 12 carbon cyclic ring, optionally containing alkyl pendants; and the number of carbon atoms in R, $R^1$, $R^2$, and $R^3$ can be such that the total number of carbon atoms in the epoxide is from 4 to 50. Suitable unsaturated mono-epoxides can include, but are not limited to, 4-vinyl cyclohexene oxide, 1-methyl-4-isopropenyl cyclohexene monoxide, butadiene monoxide, or any combination thereof.

Illustrative unsaturated methylol compounds can be represented by the general Formula (IV):

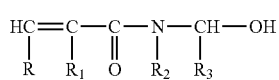

Formula (IV)

where R, $R_1$, $R_2$, and $R_3$ can independently be hydrogen or a hydrocarbyl group, e.g., an alkyl group, containing from about 1 to about 6 carbon atoms. For example, an alkyl group can include from 1 to 4 carbon atoms. In at least one example, R, $R_1$, $R_2$, and $R_3$ can each independently be methyl or hydrogen. Suitable unsaturated methylol compounds can include, but are not limited to, N-methylol acrylamide, N-methylol methacrylamide, N-methylol crotonamide, or any combination thereof. The N-methylol ethylenically unsaturated amide can be in the form of an aqueous solution.

In one or more embodiments, the unsaturated monomer can be free from any aromatic rings. Said another way, in at least one embodiment, the unsaturated monomer does not contain an aromatic ring. In one or more embodiments, the unsaturated monomer and the polyphenolic compound can be different compounds with respect to one another. Said another way, the unsaturated monomer and the polyphenolic compound are not the same compound. In at least one embodiment, the unsaturated monomer can include at least one unsaturated glycidyl ether. In at least one embodiment, the unsaturated monomer can include at least one unsaturated glycidyl ester. In at least one embodiment, the unsaturated monomer can include at least one unsaturated mono-epoxide. In at least one embodiment, the unsaturated monomer can include at least one unsaturated methylol compound. In at least one embodiment, the unsaturated monomer can include maleic anhydride.

In at least one example, the binder composition can be free or essentially free of any anionic monomers. For example, the binder composition can contain less than about 3 wt %, less than about 2.5 wt %, less than about 2 wt %, less than about 1.5 wt %, less than about 1 wt %, less than about 0.7 wt %, less than about 0.5 wt %, less than about 0.3 wt %, less than about 0.1 wt %, less than about 0.05 wt %, or less than about 0.01 wt % anionic monomers. In at least one example, the binder composition can be free or essentially free of any ionic monomers. For example, the binder composition can contain less than about 3 wt %, less than about 2.5 wt %, less than about 2 wt %, less than about 1.5 wt %, less than about 1 wt %, less than about 0.7 wt %, less than about 0.5 wt %, less than about 0.3 wt %, less than about 0.1 wt %, less than about 0.05 wt %, or less than about 0.01 wt % ionic monomers. In at least one other example the binder composition can be free or essentially free of any anionic and ionic monomers. For example, the binder composition can contain less than about 3 wt %, less than about 2.5 wt %, less than about 2 wt %, less than about 1.5 wt %, less than about 1 wt %, less than about 0.7 wt %, less than about 0.5 wt %, less than about 0.3 wt %, less than about 0.1 wt %, less than about 0.05 wt %, or less than about 0.01 wt % anionic and ionic monomers. As used herein, the terms "essentially free of anionic monomers" and "essentially free of ionic monomers" means the binder composition does not include any intentionally added anionic monomers or ionic monomers, respectively. Said another way, the terms "essentially free of anionic monomers" and "essentially free of ionic monomers" means the binder composition does not contain anionic monomers or ionic monomers, respectively, but may include anionic monomers and/or ionic monomers present as an impurity.

As used herein, the term "tannin" refers to both hydrolyzable tannins and condensed tannins. As such, the binder composition can include hydrolyzable tannins, condensed tannins, or a combination of hydrolyzable tannins and condensed tannins. Illustrative genera of shrubs and/or trees from which suitable tannins can be derived can include, but are not limited to, *Acacia, Castanea, Vachellia, Senegalia, Terminalia, Phyllanthus, Caesalpinia, Quercus, Schinopsis, Tsuga, Rhus, Juglans, Carya*, and *Pinus*, or any combination thereof. In another example, genera from which suitable tannins can be derived can include, but are not limited to, *Schinopsis, Acacia*, or a combination thereof. In another example, genera from which suitable tannins can be derived can include, but are not limited to, *Pinus, Carya*, or a combination thereof.

Hydrolyzable tannins are mixtures of simple phenols such as pyrogallol and ellagic acid and of esters of a sugar, e.g., glucose, with gallic and digallic acids. Illustrative hydrolyzable tannins can include, but are not limited to, extracts recovered from *Castanea sativa*, (e.g., chestnut), *Terminalia* and *Phyllantus* (e.g., myrabalans tree species), *Caesalpinia coriaria* (e.g., divi-divi), *Caesalpinia spinosa*, (e.g., tara), algarobilla, valonea, and *Quercus* (e.g., oak). Condensed tannins are polymers formed by the condensation of flavans. Condensed tannins can be linear or branched molecules. Illustrative condensed tannins can include, but are not limited to *Acacia mearnsii* (e.g., wattle or mimosa bark extract), *Schinopsis* (e.g., quebracho wood extract), *Tsuga* (e.g., hemlock bark extract), *Rhus* (e.g., sumach extract), *Juglans* (e.g., walnut), *Carya illinoinensis* (e.g., pecan), and *Pinus* (e.g., Radiata pine, Maritime pine, bark extract species).

The condensed tannins typically include about 70 wt % to about 80 wt % active phenolic ingredients (the "tannin fraction") and the remaining ingredients (the "non-tannin fraction") typically include, but are not limited to, carbohydrates, hydrocolloid gums, and amino and/or imino acid fractions. The condensed tannins can be used as recovered or extracted from the organic matter or the condensed tannins can be purified, e.g., about 95 wt % or more active phenolic ingredients. Hydrolyzable tannins and condensed tannins can be extracted from the starting material, e.g., trees and/or shrubs, using well established processes. A more detailed discussion of tannins is discussed and described in the *Handbook of Adhesive Technology*, Second Edition, CRC Press, 2003, chapter 27, "Natural Phenolic Adhesives I: Tannin," and in *Monomers, Polymers and Composites from Renewable Resources*, Elsevier, 2008, chapter 8, "Tannins: Major Sources, Properties and Applications."

The condensed tannins can be classified or grouped into one of two main categories, namely, those containing a resorcinol unit and those containing a phloroglucinol unit. Illustrative tannins that include the resorcinol unit include, but are not limited to, black wattle tannins and quebracho tannins. The resorcinol unit can be represented by Formula V below.

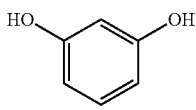

Formula V

The resorcinol group is shown within the box overlaying the unit structure of black wattle and quebracho tannins in Formula VI below. For simplicity, the structure of black wattle and quebracho tannins is represented by their flavonoid unit structure.

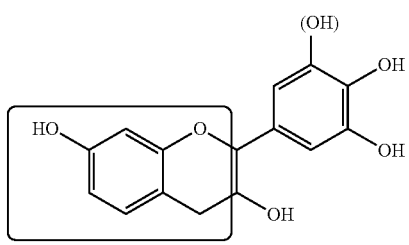

Formula VI

Illustrative tannins that include the phloroglucinol unit include, but are not limited to, pecan tannins and pine tannins. The phloroglucinol unit can be represented by Formula VII below.

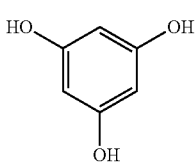

Formula VII

The phloroglucinol unit is shown within the box overlaying the unit structure of pecan and pine tannins in Formula VIII below. For simplicity, the structure of pecan and pine tannins is represented by their flavonoid unit structure.

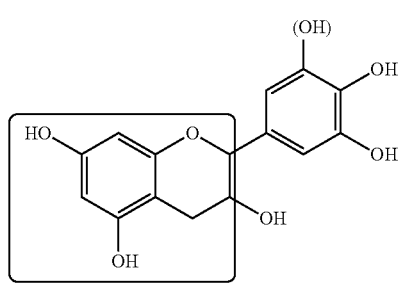

Formula VIII

Phloroglucinol is known for higher reactivity than resorcinol. As such, tannins that include the phloroglucinol unit are more reactive than tannins that include the resorcinol unit.

The tannins can have an acidic pH. For example, the pH of the tannins can be from a low of about 3, about 3.5, or about 4 to a high of about 5, about 5.5, about 6, or about 6.5. The tannins can have resorcinol and/or phloroglucinol functional groups. Suitable, commercially available tannins can include, but are not limited to, black wattle tannin, quebracho tannin, hemlock tannin, sumach tannins, pecan tannin, mimosa tannin, pine tannins, or any combination thereof.

If the binder composition includes a mixture of two different tannins, the two tannins can be present in any ratio with respect to one another. For example, a binder composition that includes a first tannin and a second tannin, where the first and second tannins are different from one another, can have a concentration of the first tannin from about 1 wt % to about 99 wt % and conversely about 99 wt % to about 1 wt % of the second tannin, based on the combined weight of the first and second tannins. In another example, the amount of the first tannin in a binder composition that includes a first and second tannin can be from a low of about 1 wt %, about 5 wt %, about 10 wt %, about 15 wt %, about 20 wt %, about 25 wt % about 30 wt %, about 35 wt %, about 40 wt %, or about 45 wt % to a high of about 60 wt %, about 65 wt %, about 70 wt %, about 75 wt %, about 80 wt %, about 85 wt %, about 90 wt %, about 95 wt %, or about 99 wt %, based on the combined weight of the first and second tannins. The binder composition can include any number of different tannins with the different tannins present in any desired amount. It should be appreciated that if the binder composition includes two or more unsaturated monomers, two or more lignins, two more novolac resins, two or more modified phenol formaldehyde resins, and/or two or more humic acids, they can be present in the same or similar amounts with respect to one another as the first and second tannin. For example, if the binder composition includes a first and second unsaturated monomer, the concentration of the first unsaturated monomer can be from about 1 wt % to about 99 wt % and conversely about 99 wt % to about 1 wt % of the second unsaturated monomer, based on the combined weight of the first and second unsaturated monomer. As such, the amount of the first unsaturated monomer in a binder composition that includes a first and second unsaturated monomer can be from a low of about 1 wt %, about 5 wt %, about 10 wt %, about 15 wt %, about 20 wt %, about 25 wt % about 30 wt %, about 35 wt %, about 40 wt %, or about 45 wt % to a high of about 60 wt %, about 65 wt %, about 70 wt %, about 75 wt %, about 80 wt %, about 85 wt %, about 90 wt %, about 95 wt %, or about 99 wt %, based on the combined weight of the first and second unsaturated monomers.

The lignin is a polymeric substance that can include substituted aromatics found in plant and vegetable matter associated with cellulose and other plant constituents. Illustrative plant and vegetable matter can include, but is not limited to, straw, hemp, sisal, cotton stalk, wheat, bamboo, sabai grass, rice straw, banana leaves, paper mulberry (i.e., bast fiber), abaca leaves, pineapple leaves, esparto grass leaves, fibers from the genus Hesperaloe in the family Agavaceae jute, salt water reeds, palm fronds, flax, ground nut shells, hardwoods, softwoods, recycled fiberboards such as high density fiberboard, medium density fiberboard, low density fiberboard, oriented strand board, particleboard, or any combination thereof. For example, the plant matter can be or include wood, for example hardwoods, softwoods, or a combination thereof. Illustrative types of wood can include, but are not limited to, alder, ash, aspen, basswood, beech, birch, cedar, cherry, cottonwood, cypress, elm, fir, gum, hackberry, hickory, maple, oak, pecan, pine, poplar, redwood, sassafras, spruce, sycamore, walnut, and willow.

The lignin can be extracted or otherwise recovered from the plant and/or vegetable matter using any suitable process or combination of processes. For example, in the pulp and paper industry, lignin-containing materials such as wood, straw, corn stalks, bagasse, and other vegetable and plant tissues are processed to recover the cellulose or pulp. As such, the residual pulping liquors that include the lignin as a by-product can be a source of lignin. There can be variation in the chemical structure of lignin. The variation in the chemical structure of lignin can depend, at least in part, on the particular plant from which the lignin is recovered from, location the plant was grown, and/or on the particular method used in recovery or isolation of the lignin from the plant and/or vegetable matter. Lignin can include active groups, such as active hydrogens and/or phenolic hydroxyl groups through which crosslinking or bridging can be effected.

Since the lignin separated from the plant may be chemically altered somewhat from that found in the plant, the term "lignin," can also refer to lignin products obtained upon separation from the cellulose or recovered from the plant matter. For example, in a sulfite pulping process, the lignocellulose material can be digested with a bisulfite or sulfite resulting in the at least partial sulfonation of the lignin. As such, the lignin can optionally be subjected to further cleavage or modifications such as alkaline treatment or reaction with other constituents to decrease the sulfonate or sulfur content and/or increase the active groups. For example, the lignin can be processed such that it has a phenolic hydroxyl content from about 1.5 wt % to about 5 wt % and less than about 3 wt % sulfonate sulfur. In other methods of recovery or separation of lignin from plant tissue, the lignin may not be sulfonated, but could be chemically altered somewhat in some other manner. For example, in residual pulping liquors obtained in sulfate or other alkaline pulping processes, the lignin can be present as an alkali metal salt dissolved in the alkaline aqueous liquor and can generally include a sufficient phenolic hydroxyl content to require no further modification. However, the alkali or kraft lignin can be further reacted with other constituents to further increase the active groups. "Hydrolysis lignin" that can be recovered from the hydrolysis of lignocellulose materials in the manufacture of sugar, for example, can also be altered somewhat from that found in the plant. As such hydrolysis lignin can be further modified to solubilize the lignin as well as to increase the phenolic hydroxyl content. Also, the lignin products such as residual pulping liquor may be subjected to various treatments such as, for example, acid, alkaline or heat treatments or reacted with the other chemicals which may further alter somewhat the lignin constituents.

The residual pulping liquors or the lignin products produced in the separation or recovery of lignin from the plant matter can include lignin of various molecular weights ranging form about 300 to over 100,000. The liquors from which the lignin can be recovered can also include one or more other constituents in addition to the lignin. For example, in the sulfite pulping process, the spent sulfite liquor can include lignosulfonates that can be present as salts of cations, such as magnesium, calcium, ammonium, sodium and/or other cations. The spent sulfite liquor solids can include about 40 wt % to about 65 wt % lignosulfonates with the remainder being carbohydrates and other organic and inorganic constituents dissolved in the liquor. Lignin products produced by other pulping processes can also include other materials such as carbohydrates, degradation products of carbohydrates, and resinous materials which are separated from the cellulosic materials with the lignin. It should be noted that it is not necessary to separate the lignin from the other constituents that can be present.

Suitable lignin material can include, but is not limited to, lignin in its native or natural state, i.e., non-modified or unaltered lignin, lignosulfonates, or any combination or mixture thereof. Suitable lignosulfonates can include, but are not limited to, ammonium lignosulfonate, sodium lignosulfonate, calcium lignosulfonate, magnesium lignosulfonate, or any combination or mixture thereof.

Suitable processes for isolating or otherwise separating lignin or lignin containing products form wood, plant, vegetable, or other lignin containing matter can include those discussed and described in U.S. Pat. Nos. 1,856,567; 2,525,433; 2,680,113; 2,690,973; 3,094,515; 3,158,520; 3,503,762; 3,585,104; 3,726,850; 3,769,272; 3,841,887; 4,100,016; 4,131,564; 4,184,845; 4,308,203; 4,355,996; 4,470,876; 4,740,591; and 4,764,596; U.S. Patent Application Publication Nos.: 2011/0294991; and WO Publication Nos. WO1992/018557A1, WO1993/021260A2; WO1994/024192A1; WO2005/062800A2; WO2006/031 175 A1; and WO2011/150508. Commercially available lignin can include, but is not limited to, lignosulfonates available from Tembec (Canada).

The novolac resin can be produced by reacting a phenol component with an aldehyde component or aldehyde compound(s) in the presence of an acid catalyst. The phenol component of the novolac resin can include a variety of substituted phenolic compounds, unsubstituted phenolic compounds, or any combination of substituted and/or unsubstituted phenolic compounds. For example, the phenol component can be phenol itself, i.e., mono-hydroxy benzene. Examples of substituted phenols can include, but are not limited to, alkyl-substituted phenols such as the cresols and xylenols; cycloalkyl-substituted phenols such as cyclohexyl phenol; alkenyl-substituted phenols; aryl-substituted phenols such as p-phenyl phenol; alkoxy-substituted phenols such as 3,5-dimethyoxyphenol; aryloxy phenols such as p-phenoxy phenol; and halogen-substituted phenols such as p-chlorophenol. Dihydric phenols such as catechol, resorcinol, hydroquinone, bis-phenol A and bis-phenol F also can also be used. Specific examples of suitable phenolic compounds (phenol components) for replacing a portion or all of the phenol used in preparing a novolac resin can include, but are not limited to, bis-phenol A, bis-phenol F, o-cresol, m-cresol, p-cresol, 3,5-5 xylenol, 3,4-xylenol, 3,4,5-trimethylphenol, 3-ethyl phenol, 3,5-diethyl phenol, p-butyl phenol, 3,5-dibutyl phenol, p-amyl phenol, p-cyclohexyl phenol, p-octyl phenol, 3,5 dicyclohexyl phenol, p-phenyl phenol, p-phenol, 3,5-dimethoxy phenol, 3,4,5 trimethoxy phenol, p-ethoxy phenol, p-butoxy phenol, 3-methyl-4-methoxy phenol, p-phenoxy phenol, naphthol, anthranol and substituted derivatives thereof. Preferably, about 80 wt % or more, about 90 wt % or more, or about 95 wt % or more of the phenol component includes phenol (mono-hydroxy benzene).

Illustrative aldehyde compounds can include the so-called masked aldehydes or aldehyde equivalents, such as acetals or hemiacetals. Suitable aldehydes can be represented by the general Formula R'CHO, where R' is a hydrogen or a hydrocarbon radical generally having 1-8 carbon atoms. Specific examples of suitable aldehyde compounds can include, but are not limited to, formaldehyde, acetaldehyde, propionaldehyde, butyraldehyde, furfuraldehyde, benzaldehyde, or any combination thereof. As used herein, the term "formaldehyde" can refer to formaldehyde, formaldehyde derivatives, other aldehydes, or combinations thereof. Preferably, the aldehyde component is formaldehyde. One or more difunctional aldehydes can also be used to produce the novolac resin, and could advantageously be used to introduce cross-links ultimately into the at least partially cured binder composition.

The aldehyde can be used in many forms such as solid, liquid, and/or gas. Considering formaldehyde in particular, the formaldehyde can be or include paraform (solid, polymerized formaldehyde), formalin solutions (aqueous solutions of formaldehyde, sometimes with methanol, in 37 percent, 44 percent, or 50 percent formaldehyde concentrations), Urea-Formaldehyde Concentrate ("UFC"), and/or formaldehyde gas in lieu of or in addition to other forms of formaldehyde can also be used. In another example, the aldehyde can be or include a pre-reacted urea-formaldehyde mixture having a urea to formaldehyde weight ratio of about 1:2 to about 1:3.

A molar ratio of formaldehyde to phenol used to produce the novolac resin can be from about 0.5 to about 0.95 or more preferably from about 0.7 to about 0.85. The reaction between the phenol and the formaldehyde to produce the novolac resin can be carried out in the presence of an acid catalyst under acidic conditions. Suitable acid catalysts can include, but are not limited to, oxalic acid, sulfuric acid, p-toluene sulfuric acid, hydrochloric acid, salicylic acid, mineral acids and salts thereof, or any combination thereof. Mixed catalyst systems, such as ZnOAc/oxalic acid and other divalent metal compounds, e.g., acetates, can be used to prepare "high-ortho" novolac resins. Divalent metal compounds can include Ca, Mg, Zn, Cd, Pb, Cu, CO, and Ni. Preferred catalysts include oxalic acid, sulfuric acid, p-toluene sulfonic acid, and ZnOAc/oxalic acid. Most preferably, the catalyst is oxalic acid or ZnOAc/oxalic acid.

The amount of acid catalyst used to produce the novolac resin can be sufficient to catalyze the reaction between the phenol and formaldehyde to produce the novolac resin. The phenol/formaldehyde reaction can be conducted in about 1 to about 6 hours, e.g., in about 2 to about 4 hours. The phenol/formaldehyde reaction can be carried out at a temperature from about 80° C. to about 100° C., e.g., about 95° C. to about 100° C. The reaction can be carried out at atmospheric pressure, although increased pressure can be utilized to permit the application of higher temperatures and, therefore, faster reaction rates and accordingly shorter reaction times.

The novolac resin can be treated to remove water and/or other volatile organic materials by heating, such as by distillation. After this treatment, the free phenol can be about 0.001% to about 2.0%, preferably about 0.001% to about 0.5%. Distillation of the resulting novolac resin can be performed at atmospheric pressure by heating up to about 140° C., and then under a vacuum until the resin reaches a temperature of about 180° C. to about 220° C. Other suitable methods for treating the resin via heat can include thin-film evaporators. The resulting molten novolac resin can be cooled to a temperature below about 100° C.

If desired, the novolac resin can be neutralized. Neutralization of the novolac resin can be accomplished by the addition of one or more bases or base compounds, such as sodium hydroxide and/or potassium hydroxide, or its equivalent. The base compound can be added in an amount sufficient to raise the pH of the novolac resin to between about 5 to about 9, e.g., about 6 to about 8. Typically, about 10 wt % to about 30 wt % of water, based on the total resin solids, can be added. Suitable novolac resins and inverted novolac resins can be as discussed and described in U.S. Pat. No. 5,670,571 and U.S. Patent Application Publication No. 2008/0280787.

Illustrative modified phenol formaldehyde resins can include ARYLZENE®, which can be represented by the general Formula IX:

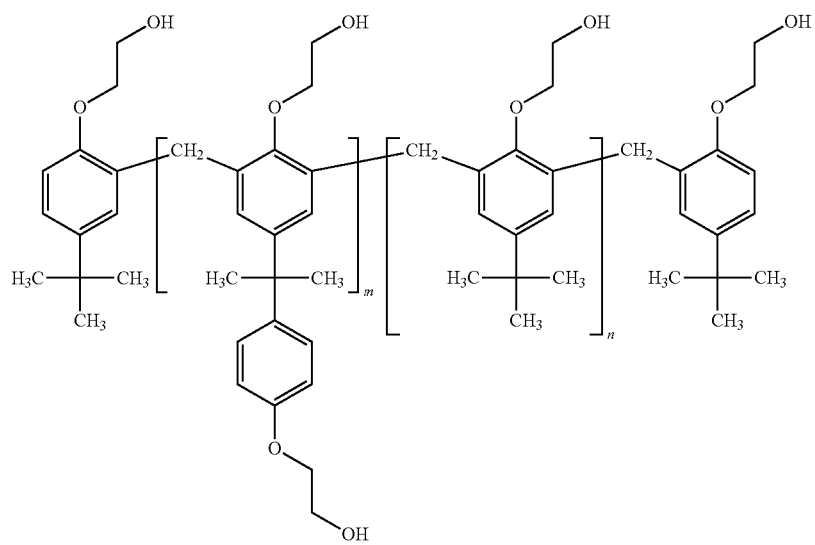

where n = 3 and 0.8 < m < 1.5

Other illustrative modified phenol formaldehyde resins can be or include those discussed and described in U.S. Pat. Nos. 5,674,970; 5,739,259; 5,756,642; 5,756,655; 5,770,750; 5,773,552; 5,837,798; 5,889,137; 6,166,151; 6,291,077; 6,399,740; and 6,569,953.

Humic acid can be represented by the general Formula X:

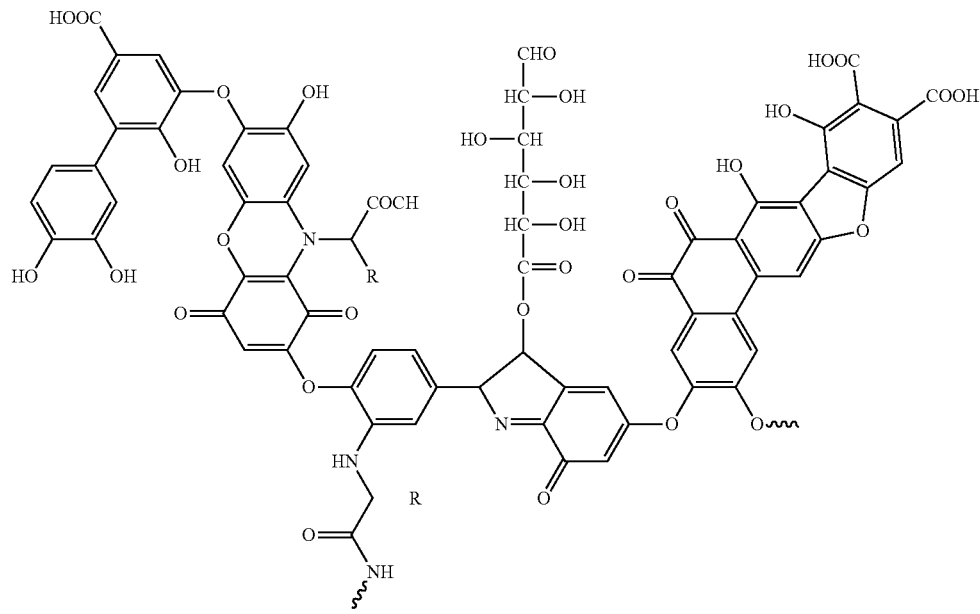

where R is independently selected from hydrogen, an alkyl, an aryl, or an aralkyl. The structure of humic acid is not fully known or understood. Additional discussion on humic acid can be found in E. M. Peña-Méndez, J. Patoča, J. Havel, "Humic substances—compounds of still unknown structure: applications in agriculture, industry, environment, and biomedicine" (Review), J. Appl. Biomed. 2004. Further discussion on humic acid can include the references referred to in the E. M. Peña-Méndez et al. article such as Stenson et al., "Copper: Ionization and fragmentation of humic substances in electrospray ionization Fourier transform-ion cyclotron resonance mass spectrometry," Anal. Chem. 74: 4397.4409, 2002; Stenson et al., "Copper: Exact masses and chemical formulas of individual suwannee river fulvic acids from ultrahigh resolution ESI FT-ICR mass spectra," Anal. Chem. 75: 1275.1284, 2003; Kujawinski et al., "High resolution fourier transform ion cyclotron resonance mass spectrometry of humic and fulvic acids: improvements and comparisons," Anal. Chem. 74: 413.419, 2002a; Kujawinski et al., "The application of electrospray ionization mass spectrometry to the structural characterization of natural organic matter," Org. Geochem. 33: 171.180, 2002b; Pokorna et al., "Characterization of humic acids by capillary zone electrophoresis and matrix assisted laser desorption ionisation time of flight mass spectrometry," In Ghabbour E. A. and G. Davies (eds.): Understanding Humic Substances:

Advanced Methods, Properties and Applications. RSC, Cambridge 1999; Brown et al., "Effect of experimental parameters on the ESI FT-ICR mass spectrum of fulvic acid," Anal. Chem. 72:384.390, 2000; and Gajdošová et al. "Mass spectrometry and capillary electrophoresis analysis of Coal Derived Humic Acids Produced from Oxyhumolite. A comparative Study," Humic Substances. Versatile components of plants, soils and water (E. A. Ghabbour, G. Davies, Eds), The Royal Society of Chemistry (RSC), Cambridge 2000.; Pokorná et al., "Analysis and characterization of a 'Standard' coal derived Humic Acid, Humic Substances," in: Versatile components of plants, soils and water (E. A. Ghabbour, G. Davies, Eds), The Royal Society of Chemistry (RSC), Cambridge 2000.

The polyphenolic compound can be combined with a liquid medium. Illustrative liquid mediums can include, but are not limited to, water, alcohols, glycols, acetonitrile, or any combination thereof. Suitable alcohols can include, but are not limited to, methanol, ethanol, propanol, butanol, or any combination thereof. Suitable glycols can include, but are not limited to, ethylene glycol, propylene glycol, or a combination thereof. As used herein, the terms "aqueous medium" and "aqueous liquid" can be or include water and/or mixtures composed of water and/or other water-miscible solvents. Illustrative water-miscible solvents can include, but are not limited to, alcohols, ethers, amines, other polar aprotic solvents, and the like. The tannin, lignin, and/or novolac resin, if combined with a liquid medium, can have a solids concentration from a low of about 1 wt %, about 5 wt %, about 10 wt %, about 20 wt %, or about 30 wt % to a high of about 60 wt %, about 70 wt %, about 80 wt %, about 90 wt %, about 95 wt %, or about 99 wt %. For example, the tannin, lignin, and/or novolac resin mixture, if combined with a liquid medium, can have a solids concentration from about 10 wt % to about 70 wt %, about 20 wt % to about 50 wt %, or about 5 wt % to about 60 wt %.

As used herein, the solids content of the polyphenolic compound, as understood by those skilled in the art, can be measured by determining the weight loss upon heating a small sample, e.g., 1-5 grams of the lignin, tannin, and/or novolac resin, to a suitable temperature, e.g., 125° C., and a time sufficient to remove any liquid combined therewith. By measuring the weight of the sample before and after heating, the percent solids in the sample can be directly calculated or otherwise estimated.

An exemplary reaction between glycidyl methacrylate and tannin can be represented by the following equation (equation I) showing the formation of an illustrative modified tannin.

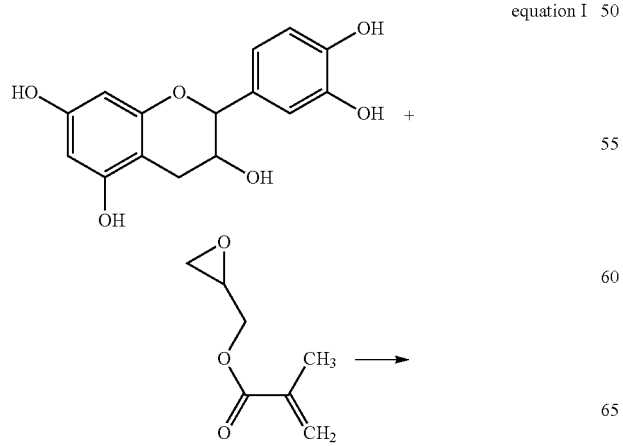

equation I

An exemplary reaction between allyl-glycidyl ether and tannin can be represented by the following equation (equation II) showing the formation of an illustrative modified tannin.

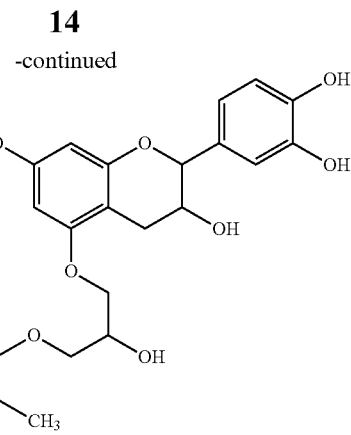

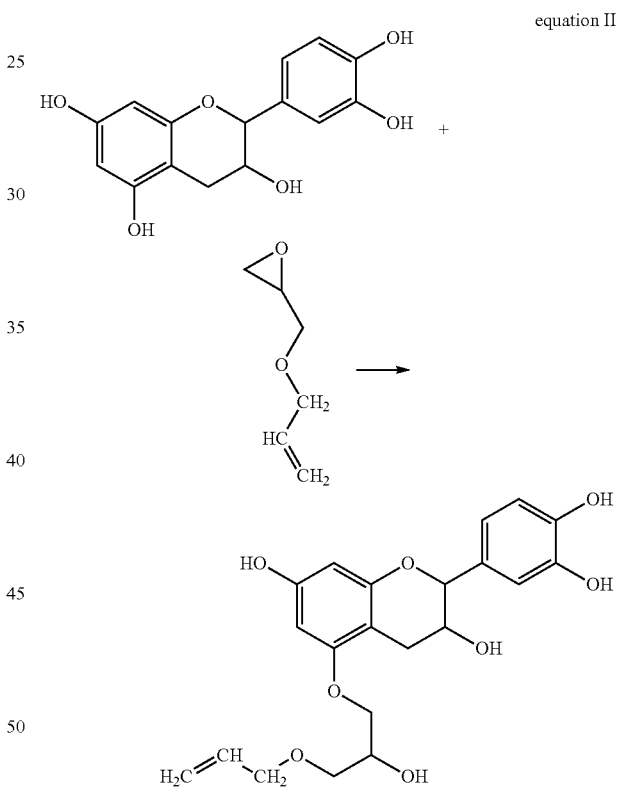

equation II

The at least partial reaction between the unsaturated monomer and the lignin, tannin, novolac resin, modified phenol formaldehyde resin, bis-phenol A, humic acid, or any combination thereof to produce the binder composition can be carried out under any suitable process conditions. As used herein, the term "reaction mixture" can refer to the mixture of the one or more unsaturated monomers mixed, blended, or otherwise combined with at least one of the lignin, tannin, novolac resin, modified phenol formaldehyde resin, bis-phenol A, humic acid. The reaction product of the unsaturated monomer and the lignin, tannin, and/or novolac can also be referred to as a modified lignin, modified tannin, modified novolac resin. The at least partial reaction between the unsaturated monomer and the lignin, tannin, novolac resin, or any combination thereof can form one or more new covalent bonds between the unsaturated monomer and the lignin, tannin, novolac resin, or any combination thereof.

The amount of the unsaturated monomer in the reaction mixture can widely vary. For example, the amount of the unsaturated monomer in the reaction mixture can be from about 0.1 wt % to about 50 wt %, based on the solids weight of the polyphenolic compound. In another example, amount of the unsaturated monomer in the reaction mixture can be from a low of about 0.05 wt %, about 0.1 wt %, about 0.5 wt %, about 1 wt %, about 2 wt %, about 3 wt %, about 5 wt %, or about 10 wt % to a high of about 20 wt %, about 30 wt %, about 40 wt %, or about 50 wt %, based on the solids weight of the polyphenolic compound. In another example, the amount of the unsaturated monomer in the reaction mixture can be from a low of about 0.1 wt %, about 0.3 wt %, about 0.5 wt %, about 0.7 wt %, or about 1 wt % to a high of about 3 wt %, about 5 wt %, about 7 wt %, about 8.5 wt %, or about 10 wt %, based on the solids weight of the polyphenolic compound. In another example, the amount of the unsaturated monomer in the reaction mixture can be from a low of about 10 wt %, about 15 wt %, about 20 wt %, or about 25 wt % to a high of about 30 wt %, about 35 wt %, about 40 wt %, or about 45 wt %, based on the solids weight of the polyphenolic compound. In another example, the amount of the unsaturated monomer in the reaction mixture can be from about 1 wt % to about 8 wt %, about 0.2 wt % to about 3 wt %, about 3 wt % to about 9 wt %, about 3.5 wt % to about 7.5 wt %, or about 4 wt % to about 8.5 wt %, based on the solids weight of the polyphenolic compound. In another example, the amount of the unsaturated monomer in the reaction mixture can be from about 1 wt % to about 4 wt %, about 1.5 wt % to about 3 wt %, about 2 wt % to about 2.5 wt %, or about 1.8 wt % to about 2.4 wt %, based on the solids weight of the polyphenolic compound. In another example, the amount of the unsaturated monomer in the reaction mixture can be at least 1 wt %, at least 3 wt %, at least 5 wt %, at least 7 wt %, at least 10 wt %, at least 12 wt %, at least 15 wt %, at least 17 wt %, at least 20 wt %, at least 23 wt %, at least 25 wt %, at least 28 wt %, at least 30 wt %, at least 33 wt %, or at least 35 wt % and up to about 40 wt %, about 45 wt %, or about 50 wt %, based on the solids weight of the polyphenolic compound. In another example, the amount of the unsaturated monomer in the reaction mixture can be less than 50 wt %, less than 45 wt %, less than 40 wt %, less than 35 wt %, less than 30 wt %, less than 25 wt %, less than 20 wt %, less than 15 wt %, or less than 12 wt % and greater than about 0.1 wt % greater than about 0.5 wt %, greater than about 1 wt %, greater than about 2 wt %, greater than about 3 wt %, greater than about 5 wt %, or greater than about 7 wt %, based on the solids weight of the polyphenolic compound. In one or more embodiments, a weight ratio between the unsaturated monomer and the polyphenolic compound, on a solids basis, can be from a low of about 0.001:100, about 0.01:1,000, about 0.1:100, about 1:800, about 1:500, about 1:300, about 1:150, about 1:100, about 1:90, or about 1:80 to a high of about 1:70, about 1:50, about 1:40, about 1:30, about 1:20, about 1:10, about 1:5, about 1:3, or about 1:2. For example, the weight ratio of the unsaturated monomer to the polyphenolic compound, on a solids basis, can be from about 1:1000 to about 1:2, about 1:200 to about 1:3, about 1:2 to about 1:15, about 1:5 to about 1:100, about 1:10 to about 1:75, about 1:50 to about 1:500, about 1:8 to about 1:15, about 1:7 to about 1:20, or about 1:6 to about 1:25.

The temperature of the reaction mixture during the reaction can be from a low of about 0° C., about 10° C., about 20° C., about 25° C., or about 35° C. to a high of about 80° C., about 90° C., about 100° C., about 125° C., or about 150° C. For example, the reaction mixture can be heated to a temperature of about 30° C. to about 95° C., about 50° C. to about 70° C., about 45° C. to about 85° C., or about 55° C. to about 115° C. The reaction can be carried out under a vacuum, at atmospheric pressure, or at a pressure greater than atmospheric pressure. For example, the reaction can be carried out at a pressure from a low of about 25 kPa, about 50 kPa, about 75 kPa, or about atmospheric pressure to a high of about 150 kPa, about 500 kPa, about 1,000 kPa, or about 2,000 kPa.

The components of the binder composition, i.e., the unsaturated monomer and at least one of the lignin, tannin, novolac resin, modified phenol formaldehyde resin, bisphenol A, humic acid, can be at least partially reacted in any device, system, apparatus, or combination of devices, systems, and/or apparatus. For example, the components of the binder composition can be mixed, blended, or other wise combined with one another and allowed to at least partially react to produce the binder composition. Illustrative mixing, blending, or other combining device, system, apparatus, or combination thereof, which can be referred to as "mixing equipment," can include, but is not limited to, mechanical mixer agitation, ejectors, static mixers, mechanical/power mixers, shear mixers, sonic mixers, or combinations thereof. One or more heating jackets, heating coils, internal heating elements, cooling jacks, cooling coils, internal cooling elements, or the like, can be used to adjust or otherwise control the temperature of the reaction mixture. The reaction of components of the binder composition can be carried out in an open vessel and/or an enclosed vessel.

The pH of the reaction mixture can be acidic, neutral, or basic. For example, the pH of the reaction mixture can be from a low of about 2, about 4, or about 6 to a high of about 8, about 10, or about 12. As such, the binder composition can have a pH from a low of about 2, about 4, or about 6 to a high of about 8, about 10, or about 12. The pH of the binder composition can be adjusted to any desired pH by adding one or more base compounds or one or more acid compounds thereto. The unsaturated monomer and the lignin, tannin, and/or novolac resin can be reacted with one another for a time from a low of about 5 minutes, about 15 minutes, or about 30 minutes to a high of about 1 hour, about 2 hours, about 3 hours, or about 5, for example.

Illustrative base compounds that can be used to adjust the pH of the reaction mixture and/or the binder composition can include, but are not limited to, hydroxides, carbonates, ammonia, amines, amides, or any combination thereof. Illustrative hydroxides can include, but are not limited to, sodium hydroxide, potassium hydroxide, ammonium hydroxide (e.g., aqueous ammonia), lithium hydroxide, and cesium hydroxide. Illustrative carbonates can include, but are not limited to, sodium carbonate, sodium bicarbonate, potassium carbonate, and ammonium carbonate. Illustrative amines can include, but are not limited to, trimethylamine, triethylamine, triethanolamine, diisopropylethylamine (Hunig's base), pyridine, 4-dimethylaminopyridine (DMAP), and 1,4-diazabicyclo[2.2.2]octane (DABCO).

Illustrative acid compounds that can be used to adjust the pH of the reaction mixture and/or the binder composition can include, but are not limited to, one or more mineral acids, one or more organic acids, one or more acid salts, or any combination thereof. Illustrative mineral acids can include, but are not limited to, hydrochloric acid, nitric acid, phosphoric acid, sulfuric acid, or any combination thereof. Illustrative organic acids can include, but are not limited to, acetic acid, formic acid, citric acid, oxalic acid, uric acid, lactic acid, or any combination thereof. Illustrative acid salts can include, but are not limited to, ammonium sulfate, sodium bicarbonate, sodium hydrosulfide, sodium bisulfate, sodium metabisulfite, or any combination thereof.

The binder composition produced by at least partially reacting the unsaturated monomer with the polyphenolic compound mixed with a liquid medium can have a total concentration of solids from about 1 wt % to about 99 wt %, based on the combined weight of the tannin, lignin, novolac resin, unsaturated monomer, and liquid medium. In other words, the binder composition can have a solids content of about 100 wt % or if combined with a liquid medium anywhere from about 1 wt % to about 99 wt %. For example, the binder composition can have a solids content of about 5 wt % to about 25 wt %, about 10 wt % to about 40 wt %, about 20 wt % to about 60 wt %, about 30 wt % to about 80 wt %, about 45 wt % to about 95 wt %, about 15 wt % to about 35 wt %, about 7 wt % to about 27 wt %, about 13 wt % to about 33 wt %, about 25 wt % to about 85 wt %, about 60 wt % to about 85 wt %, or about 65 wt % to about 95 wt %. In one or more embodiments, the binder composition can have a water concentration from a low of about 1 wt %, about 5 wt %, about 10 wt %, about 15 wt %, about 20 wt %, about 25 wt %, about 30 wt %, about 35 wt %, about 40 wt %, about 45 wt %, about 50 wt %, or about 55 wt % to a high of about 60 wt %, about 65 wt %, about 70 wt %, about 75 wt %, or about 80 wt %, based on a solids weight of the polyphenolic compound.

The binder composition can have a viscosity form a low of about 100 centipoise ("cP"), about 500 cP, about 1,000 cP, or about 1,500 cP to a high of about 3,000 cP, about 5,000 cP, about 8,500 cP, or about 10,000 cP. Preferably the viscosity of the binder composition is less than about 10,000 cP, less than about 8,000 cP, less than about 6,500 cP, or less than about 5,000 cP. The binder composition can be determined using a Brookfield Viscometer at a temperature of 25° C.

The binder compositions discussed and described herein can be used in the production or preparation of a variety of composite lignocellulose containing products. For example, the binder composition can be applied to a plurality of lignocellulose substrates that can be formed into a desired shape before or after application of the binder composition, and the binder composition can be at least partially cured to produce a composite product. The lignocellulose substrates can include any one or more of the plant and vegetable materials discussed and described above with reference to the source for the lignin. As used herein, the term "lignocellulose" refers to a material that includes lignin, cellulose, hemicelluose, or any combination thereof.

The starting material, from which the substrates can be derived from, can be shaped, reduced, or otherwise formed to the appropriate dimensions by various processes such as hogging, grinding, hammer milling, tearing, shredding, and/or flaking. Other processes for producing the substrates can include skiving, cutting, slicing, and/or sawing. Suitable forms of the lignocellulose substrates can include, but are not limited to, chips, flakes, wafers, fibers, shavings, sawdust or dust, veneer, or the like. Other suitable lignocellulose substrates can include, but are not limited to, wood chips, wood fibers, wood flakes, wood strands, wood wafers, wood shavings, wood particles, wood veneer, or any combination thereof.

The particular configuration of the substrates can be based, at least in part, on the desired product. For example, particulates such as chips, fibers, shavings, sawdust or dust, or the like can be preferred for producing particleboards, fiberboards, and the like. The particulates can have a length from a low of about 0.05 mm, about 0.1 mm, about 0.2 mm to a high of about 1 mm, about 5 mm, about 10 mm, about 20 mm, about 30 mm, about 40 mm, about 50 mm, or about 100 mm. In another example, veneers, i.e., layers or sheets of wood, can be used for producing plywood, laminated veneer lumber, and the like. The veneers can have a thickness from a low of about 0.8 mm, about 0.9 mm, about 1 mm, about 1.1 mm or about 1.2 mm to a high of about 3 mm, about 4 mm, about 5 mm, about 6 mm, about 7 mm, about 8 mm, about 9 mm, or about 10 mm.

The lignocellulose substrates can include liquid on, about, and/or within the substrates. For example, the lignocellulose substrates can have a moisture concentration from a low of about 1 wt % to a high of about 170 wt %, based on a dry weight of the lignocellulose substrate. The lignocellulose substrates can be fresh, i.e., not treated or dried, or dried and/or treated. For example, the lignocellulose substrates and/or the starting material from which the lignocellulose substrates were derived can be at least partially dried. In another example, the lignocellulose substrates can be washed and/or leached with an aqueous medium such as water.

Illustrative composite products that can be produced with the binder compositions discussed and described herein can include, but are not limited to, particleboard, fiberboard such as medium density fiberboard ("MDF") and/or high density fiberboard ("HDF"), plywood such as hardwood plywood and/or softwood plywood, oriented strand board ("OSB"), laminated veneer lumber ("LVL"), laminated veneer boards ("LVB"), engineered wood flooring, and the like. The binder compositions can also be used to bond or otherwise join two or more pieces of lumber to produce a finished product such as wood doors, wood furniture, and the like.

The lignocellulose substrate can be at least partially oxidized prior to contact with the binder composition and/or after contact with the binder composition. The lignocellulose substrates and/or the starting materials from which the lignocellulose substrates can be derived can be contacted with one or more oxidants to produce an oxidized lignocellulose substrate. For example, the lignocellulose substrates and/or the starting material can be contacted with one or more oxidants under conditions sufficient to at least partially oxidize the lignin present in the lignocellulose substrate. In another example, the lignocellulose substrates and/or the starting material can be contacted with one or more oxidants under conditions sufficient to at least partially oxidize the lignin present in the lignocellulose substrates. In another example, the lignocellulose substrates can be at least partially oxidized after mixing, blending, or otherwise contacting the lignocellulose substrates with the binder composition. For example, the lignocellulose substrates can be at least partially oxidized when the mixture is heated and/or pressed to produce the composite product.

Partially oxidizing at least a portion of the lignocellulose substrates can increase the number of free radicals in the lignocellulose substrates. Increasing the number of free radicals in the lignocellulose substrates can improve the crosslinking reactions between the lignocellulose substrates and/or between the lignocellulose substrates and the binder composition. The oxidation of the lignocellulose substrates can be sufficient for water soluble reaction products with binding properties to form.

Any suitable oxidant or combination of oxidants can be used to at least partially oxidize the lignocellulose substrate. Illustrative oxidants can include, but are not limited to inorganic and/or organic peroxy compounds, ozone, ozonides, halogen containing oxidants, oxygen, or any combination thereof. In at least one example, the oxidant can be free of or essentially free of nitrogen and/or nitrogen containing compounds. For example, the oxidant can be free or essentially free of nitrates and nitroxylradicals. In another example, the oxidant can be free or essentially free of chlorates.

Illustrative inorganic peroxy compounds can include, but are not limited to, hydrogen peroxide, hydrogen peroxide generating compounds, e.g., alkali metal salts of percarbonate, perborate, peroxysulfate, peroxyphosphate, and/or peroxysilicate, and/or corresponding weak acids. Illustrative organic peroxy compounds can include, but are not limited to, peroxy carboxylic acids, e.g., t-butyl peroxide, t-butyl hydroperoxide, benzoyl peroxide, peracetic acid and/or perbenzoic acid. Illustrative halogen containing oxidants can include, but are not limited to, alkali metal chlorite, alkali metal hypochlorite, chlorine dioxide, and/or a chloro sodium salt of cyanuric acid. An illustrative ozonide can include, but is not limited to, dimethyloxirane.

The oxidant can be combined with the lignocellulose substrates in the presence of a liquid. Illustrative solvents can include, but are not limited to, water, alcohol, or a combination thereof. For example, an oxidant/lignocellulose substrate mixture can have a liquid concentration from a low of abut 1 wt %, about 10 wt %, or about 20 wt % to a high of about 50 wt %, about 70 wt %, about 80 wt %, about 90 wt %, or about 95 wt %. In at least one example, the oxidant can be or include an aqueous solution of hydrogen peroxide. The concentration of hydrogen peroxide in the aqueous solution can range form a low of about 1 wt %, about 3 wt %, or about 5 wt % to a high of about 20 wt %, about 25 wt %, or about 30 wt %.

The particular amount of oxidant combined with the lignocellulose substrates can depend, at least in part, on the particular oxidant and/or the particular lignocellulose substrate. The amount of oxidant combined with the lignocellulose substrates can be from about 1 wt % to about 200 wt %, based on the dry weight of the lignocellulose substrate. For example, the amount of oxidant combined with the lignocellulose substrates can be from a low of about 1 wt %, about 5 wt %, about 10 wt %, or about 20 wt % to a high of about 80 wt %, about 100 wt %, about 120 wt %, or about 150 wt %, based on the dry weight of the lignocellulose substrate. In one particular example, the oxidant can be or include hydrogen peroxide and the oxidant can be present in an amount from about 0.1 wt % to about 30 wt %, about 1 wt % to about 20 wt %, about 5 wt % to about 50 wt %, about 10 wt % to about 70 wt %, or about 0.5 wt % to about 25 wt %, based on the dry weight of the lignocellulose substrate.

In addition to the one or more oxidants, one or more catalysts can be combined with the oxidant/lignocellulose mixture to produce the oxidized lignocellulose substrates. The one or more oxidants and/or catalysts, if present, can be combined with the reaction product between the one or more unsaturated monomers and the one or more polyphenolic compounds to produce the binder composition.

The catalyst, if present, can be combined with the lignocellulose substrates before, after, and/or when the one or more oxidants are combined with the lignocellulose substrates. In another example, the catalyst can be combined with the reaction product between the one or more unsaturated monomers and the one or more polyphenolic compounds to produce the binder composition. The catalyst can also be referred to as an initiator, a promoter, a reducer, and/or an accelerator. Suitable catalysts can be or include, but are not limited to, metal ions, tertiary amines, polymeric tertiary amines, polyamines, phosphates, bisulfites, metabisulfites, tetraacetylethylenediamine, cyanamides, ultraviolet light, or any combination thereof. Any catalyst or combination of catalysts can be combined with the lignocellulose substrates and the oxidant to produce the mixture. In addition to or in lieu of contacting the lignocellulose substrates with an oxidant and/or catalyst, ultrasonic waves, photo-Fenton and/or electro-Fenton reactions (in situ generation of hydroxyl radicals by radiation or electric currents) can be used.

Suitable metal can include one or more Group 3 to Group 12 metal atoms. As used herein, all reference to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced there with permission from IUPAC) unless otherwise noted. Illustrative transition metals can include, but are not limited to, metal ions of iron, copper, manganese, tungsten, molybdenum, cobalt, titanium, or any combination or mixture thereof. The metal can be in the form of an oxide. The metal can be in the form of a salt or complex, e.g., bound to one or more complexing agents or compounds. Illustrative complexing agents or complexing compounds can include, but are not limited to, cyanide (CN), sulfate ($SO_4^{2-}$), ethylenediaminetetraacetic acid (EDTA), ethylenediamine-N,N'-disuccinic acid (EDDS), ethyleneglycol bis(2-aminoethyl ter)-N,N,N',N'-tetraacetic acid (EGTA), diethylenetriaminepentaacetic acid (DTPA), trans-1,2-diaminocyclohexane tetraacetic acid (CDTA), iminodisuccinate (IDS), nitrilotracetic acid (NTA), or any combination or mixture thereof. Other complexing compounds can include phosphates, or complexing agents based on phosphonic acid, oxalic acid, ascorbic acid, nitrilo acetate, gallic acid, fulvic acid, or polyoxomethalates.

In one or more embodiments, the catalyst can include $Fe^{2+}$ or $Fe^{3+}$ ions such as iron(II) sulfate, iron(II) oxide, iron(III) sulfate, iron(III) oxide. Other iron ion containing catalysts can include, but are not limited to, $[Fe(CN)_6]^{3-}$, ferrocyanide $[Fe(CN)_6]^{4-}$, and/or $[Fe(CN)_5NO]^{2-}$. For example, the catalyst can be or include, but is not limited to, potassium ferricyanide ($K_3[Fe(CN)_6]$), potassium ferrocyanide ($K_4[Fe(CN)_6]$), ammonium hexacyanoferrate(II) hydrate (($NH_4)_4[Fe(CN)_6].xH_2O$), ammonium iron(III) hexacyanoferrate(II) hydrate, sodium ferrocyanide decahydrate ($Na_4[Fe(CN)_6].10H_2O$), sodium nitroprusside dihydrate ($Na_2[Fe(CN)_5NO].2H_2O$). Other suitable catalyst that contain iron can include, but are not limited to, Fe[EDTA], Fe[EDDS], Fe[DTPA], Fe[EGTA], Fe[CDTA], Fe[IDS], or any mixture thereof. In at least one specific embodiment, the catalyst preferably includes ferricyanide, e.g., potassium ferricyanide, a complex of iron and ethylenediaminetetraacetic acid (EDTA), a complex of iron and (S,S)-ethylenediamine-N,N'-disuccinic acid ((S,S)-EDDS), a complex of iron and (R,R)-ethylenediamine-N,N'-disuccinic acid ((R,R)-EDDS), a complex of iron and (R,S)-ethylenediamine-N,N'-disuccinic acid ((R,S)-EDDS), a complex of iron and diethylenetriaminepentaacetic acid (DTPA), a complex of iron and trans-1,2-diaminocyclohexane tetraacetic acid (DCTA), a complex of iron and iminodisuccinate (IDS), or any mixture thereof.

Tertiary amines can be represented by the general Formula $NR_1R_2R_3$, where each $R_1$, $R_2$, and $R_3$ is independently selected from alkyls, cycloalkyls, heterocycloalkyls, aryls, heteroaryls, and substituted aryls. The alkyl can include branched or unbranched alkyls having from 1 to about 15 carbon atoms or more preferably from 1 to about 8 carbon atoms. Illustrative alkyls can include, but are not limited to, methyl, ethyl, n-propyl, isopropyl, n-butyl, sec butyl, t-butyl, n-pentyl, n-hexyl, and ethylhexyl. The cycloalkyls can include from 3 to 7 carbon atoms. Illustrative cycloalkyls can include, but are not limited to, cyclopentyl, substituted cyclopentyl, cyclohexyl, and substituted cyclohexyl. The term "aryl" refers to an aromatic substituent containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, phenanthrenyl, and the like. The aryl substituents can include from 1 to about 20 carbon atoms. The term "heteroatom-containing," as in a "heteroatom-containing cycloalkyl group," refers to a molecule or molecular fragment in which one or more carbon atoms is replaced with an atom other than carbon, e.g., nitrogen, oxygen, sulfur, phosphorus, boron, or silicon. Similarly, the term "heteroaryl" refers to an aryl substituent that is heteroatom-containing. The term "substituted," as in "substituted aryls," refers to a molecule or molecular fragment in which at least one hydrogen atom bound to a carbon atom is replaced with one or more substituents that are functional groups such as hydroxyl, alkoxy, alkylthio, phosphino, amino, halo, silyl, and the like. Illustrative tertiary amines can include, but are not limited to, trimethylamine, triethylamine, triethanolamine, or any combination thereof. Illustrative polymeric tertiary amines can include, but are not limited to, poly(N-methyl-diallyl amine), poly(N-dimethyl-vinyl amine), copolymers of N-dimethyl-vinyl amine, or any combination thereof. Illustrative polyamines can include, but are not limited to, diethylenetriamine ("DETA"), triethylenetetramine ("TETA"), tetraethylenepentamine ("TEPA"). Other polyamines can include, for example, 1,3-propanediamine, 1,4-butanediamine, polyamidoamines, and polyethylenimines.

Illustrative phosphates can be or include, but are not limited to, potassium, phosphate, sodium phosphate, ammonium phosphate, or any combination or mixture thereof. Illustrative bisulfites can include, but are not limited to, sodium bisulfite. Illustrative metabisulfites can be or include, but are not limited to, sodium metabisulfite, potassium metabisulfite, or any combination or mixture thereof. Illustrative cyanamides can include, but are not limited to, cyanamide, calcium cyanamide, sodium hydrogen cyanamide, or any combination thereof.

In one or more embodiments, a suitable catalyst can also include one or more azo compounds. The one or more azo compounds can be combined with the reaction product between the one or more unsaturated monomers and the one or more polyphenolic compounds to produce the binder composition. The one or more azo compounds can be combined with the lignocellulose substrates. The azo compound can be represented by the general Formula R—N=N—R', where R and R' can independently be substituted aryl or substituted alkyl. Suitable azo compounds can include, but are not limited to, azobisisobutyronitrile (AIBN).

The amount of catalyst, if present in the free radical precursor, can widely vary. For example, the amount of catalyst in the mixture can be from a low of about 0.00001 wt %, about 0.0001 wt %, about 0.001 wt %, about 0.01 wt %, or about 0.1 wt % to about 0.5 wt %, about 1 wt %, about 3 wt %, about 5 wt %, about 10 wt %, or about 20 wt %, based on the dry weight of the lignocellulose substrates. In another example, the amount of catalyst in the mixture can be from about 0.01 wt % to about 1.5 wt %, about 0.1 wt % to about 1.3 wt %, about 0.05 wt % to about 0.5 wt %, about 0.07 wt % to about 0.4 wt %, about 0.05 wt % to about 5 wt %, based on the dry weight of the lignocellulose substrates. In another example, the amount of the catalyst in the mixture can be about 0.001 wt % to about 0.5 wt %, about 0.15 wt % to about 0.35 wt %, about 0.1 wt % to about 0.4 wt %, about 0.1 wt % to about 2 wt %, about 0.05 wt % to about 3 wt %, about 0.05 wt % to about 0.35 wt %, about 0.1 wt % to about 4.5 wt %, about 0.15 wt % to about 4 wt %, about 0.05 wt % to about 3 wt %, or about 0.01 wt % to about 3.5 wt %, based on the dry weight of the lignocellulose substrates.

One or more salts can be added to the lignocellulose substrates and/or to the oxidized lignocellulose substrates. The amount of salt that can be added to the lignocellulose substrates and/or the oxidized lignocellulose substrates can be from a low of about 1 wt %, about 2 wt %, or about 3 wt % to a high of about 10 wt %, about 20 wt %, or about 30 wt %, based on the dry weight of the lignocellulose substrates and/or oxidized lignocellulose substrates. The one or more salts can be added before, after, and/or during oxidation of the lignocellulose substrates, if oxidized. Illustrative salts can include Al, Ca, K, Na, Cu, Zn, Mg, Mn, Ba, and/or Li cations. Suitable anions can be in the form of carbonates, chlorides, nitrates, silicates, acetates, formiate, sulphates, silicates, phosphates, and/or other forms.

The lignocellulose substrates can be oxidized and/or otherwise modified with the one or more compounds containing one or more aromatic groups and/or the salts under any suitable conditions. For example, the lignocellulose substrates can be oxidized at a pH from about 1 to about 12. For example the pH of the lignocellulose and oxidant mixture can range form a low of about 2, about 3, or about 4 to a high of about 8, about 9, or about 10. In another example the pH of the lignocellulose and oxidant mixture can be from about 1 to about 7, about 2 to about 6, or about 2 to about 5. The pH range can be naturally obtained and/or one or more base compounds and/or acid compounds can be added thereto in order to adjust or otherwise control the pH.

The oxidation of the lignocellulose substrates can be carried out at a temperature from a low of about 0° C. to a high of about 200° C. For example, the temperature can be from about 10° C. to about 150° C., about 20° C. to about 100° C., or about 25° C. to about 90° C. The oxidation of the lignocellulose substrates can be carried out at a pressure from a low of about 25 kPa, about 50 kPa, or about 75 kPa to a high of about 150 kPa, about 500 kPa, about 1,000 kPa, or about 2,000 kPa. In at least one example, the oxidation of the lignocellulose substrates can be carried out at atmospheric pressure.

The length of time the lignocellulose substrates can undergo the oxidation reaction can be from about 30 seconds to about 10 hours. For example, the length of time the lignocellulose substrates can be oxidized can be from a low of about 1 minute, about 5 minutes or about 10 minutes to a high of about 2 hours, about 4 hours, or about 8 hours. In at least one example, the oxidation of the lignocellulose substrates can be carried out for a length of time of at least 10 minutes, at least 15 minutes, at least 20 minutes, or at least 30 minutes.

The oxidized lignocellulose substrates can be dried after the oxidation thereof. For example, at least a portion of any water and/or other liquids present in the oxidized lignocellulose substrates can be removed via evaporation. In another example, at least a portion of any water and/or other liquids present in the oxidized lignocellulose substrates can be removed under vacuum, e.g., via vacuum distillation. The oxidized lignocellulose substrates can be stored for a period of time before use in the production of a composite lignocellulose containing substrate. For example, the oxidized lignocellulose substrates can be at least partially dried and the stored in a container for a period of time from about 1 hour, 1 day, about 3 days, or about 1 week to about 2 weeks, about 3 weeks, about 1 month, or more. Suitable oxidized lignocellulose substrates can be prepared as discussed and described in U.S. Pat. No. 7,326,317.

The production of composite lignocellulose containing products can include contacting a plurality of lignocellulose substrates and/or oxidized lignocellulose substrates and/or lignocellulose substrates mixed with the binder composition. The substrates can be contacted with the binder composition by spraying, coating, mixing, brushing, falling film or curtain coater, dipping, soaking, or the like. After contacting the plurality of substrates with the binder composition, the binder composition can be at least partially cured. As used herein, the terms "curing," "cured," "at least partially curing," "at least partially cured," and similar terms are intended to embrace the structural and/or morphological change that occurs in a the binder composition, such as by covalent chemical reaction (crosslinking), ionic interaction or clustering, improved adhesion to the substrate, phase transformation or inversion, and/or hydrogen bonding when the binder composition is at least partially cured to cause the properties of a flexible, porous substrate, such as a mat or blanket of particulates and/or a rigid or semi-rigid substrate, such as a wood or other lignocellulose containing board or sheet, to which an effective amount of the binder composition has been applied, to be altered.

At least partially curing the binder composition can include applying heat and/or pressure thereto. The binder composition can also be at least partially cured at room temperature and pressure. The substrates contacted with the binder composition can be formed into a desired shape, e.g., a board, a non-woven mat, a woven mat, or the like. The substrates contacted with the binder composition can be formed into a desired shape before, during, and/or after at least partial curing of the binder composition. Depending on the particular product, the substrates contacted with the binder composition can be pressed before, during, and/or after the binder composition is at least partially cured. For example, the substrates contacted with the binder composition can be consolidated or otherwise formed into a desired shape, if desired pressed to a particular density and thickness, and heated to at least partially cure the binder composition. In another example, a blended furnish, i.e., a mixture of the particulates and the binder composition, can be extruded through a die (extrusion process) and heated to at least partially cure the binder composition.

When the mixture is heated, the mixture can contain at least a portion of the oxidant initially added to and present in the mixture. Said another way, at least a portion of the oxidant can remain unreacted or otherwise in the same form as when combined with the additional components of the mixture. For example, if oxidant includes one or more oxidants, e.g., hydrogen peroxide ($H_2O_2$), at least a portion of the oxidant in the form of hydrogen peroxide ($H_2O_2$) can be present when heating of the mixture is initiated or started. In one or more embodiments, the mixture can contain at least 11%, at least 13%, at least 15%, at least 20%, at least 25%, at least 30%, at least 35%, at least 40%, at least 45%, at least 50%, at least 55%, at least 60%, at least 65%, or at least 70% of the total amount of oxidant initially present in the mixture, i.e., the total amount of the oxidant combined with the plurality of lignocellulose substrates when the mixture is heated. In another example, the mixture can contain from about 11% to about 95%, about 15% to about 85%, about 20% to about 90%, about 30% to about 80%, about 11% to about 100%, about 35% to about 75%, about 40% to about 70%, or about 30% to about 95% of the total amount of oxidant initially present in the mixture when the mixture is heated. In at least one specific example, if the mixture can include about 5 wt % oxidant, based on the dry weight of the lignocellulose substrates when the mixture is initially formed and when the mixture is heated to a temperature of 60° C. or more at least 11% of the oxidant can be present in the mixture. Said another way, if the mixture contains about 5 wt % of the one or more oxidant, based on the dry weight of the lignocellulose substrates, upon preparation or formation of the mixture, when heating the mixture is initiated or started, the mixture can have a oxidant concentration of at least 11% of the initial 5 wt % or 0.55 wt %, based on the dry weight of the lignocellulose substrates.

In one or more embodiments, the amount of the one or more oxidants present when the mixture is heated, e.g., to a temperature of about 60° C. to about 300° C., can be at least 0.5 wt %, at least 0.7 wt %, at least 1 wt %, at least 1.2 wt %, at least 1.5 wt %, at least 1.7 wt %, at least 2 wt %, at least 2.2 wt %, at least 2.5 wt %, at least 2.7 wt %, at least 3 wt %, at least 3.2 wt %, at least 3.5 wt %, at least 3.7 wt %, at least 4 wt %, at least 4.2 wt %, at least 4.5 wt %, at least 4.7 wt %, or at least 5 wt %, based on the dry weight of the plurality of lignocellulose substrates. For example, the amount of the one or more oxidants present when the mixture is heated can be from a low of about 1 wt %, about 1.5 wt %, about 1.6 wt %, about 1.8 wt %, or about 2.1 wt % to high of about 5 wt %, about 7 wt %, about 10 wt %, about 15 wt %, about 20 wt % or more, based on the dry weight of the plurality of lignocellulose substrates. In another example, the amount of the one or more oxidants present when the mixture is heated can be from about 1 wt % to about 10 wt %, about 1.5 wt % to about 7 wt %, about 2 wt % to about 6 wt %, about 2.5 wt % to about 8 wt %, about 3 wt % to about 5.5 wt %, about 4 wt % to about 6.5 wt %, about 2.2 wt % to about 11 wt %, or about 2.3 wt % to about 6.3 wt %, based on the dry weight of the plurality of lignocellulose substrates.

In one or more embodiments, the amount of the metal in the catalyst, if the catalyst is present in the mixture, that can remain bound to the complexing agent until the mixture is heated, e.g., to a temperature of about 60° C. to about 300° C., can be at least at least 11%, at least 13%, at least 15%, at least 20%, at least 25%, at least 30%, at least 35%, at least 40%, at least 45%, at least 50%, at least 55%, at least 60%, at least 65%, or at least 70% of the amount of metal initially present in the mixture and bound to the complexing agent. In another example, the amount of the metal in the catalyst, if the catalyst is present in the mixture, that can remain bound to the complexing agent until the mixture is heated, e.g., to a temperature of about 60° C. to about 300° C., can be about1 1% to about 95%, about 15% to about 85%, about 20% to about 90%, about 30% to about 80%, about 11% to about 100%, about 35% to about 75%, about 40% to about 70%, or about 30% to about 95% of the amount of the metal initially present in the mixture and bound to the complexing agent.

The pressure applied to the lignocellulose substrates during production of the composite product can depend, at least in part, on the particular product. For example, the amount of pressure applied to a particleboard process can be from about 1 MPa to about 5 MPa or from about 2 MPa to about 4 MPa. In another example, the amount of pressure applied to a medium density fiberboard product can be from about 2 MPa to about 7 MPa or from about 3 MPa to about 6 MPa. The temperature the product can be heated to produce an at least partially cured product can be from a low of about 100° C., about 125° C., about 150° C., or about 170° C. to a high of about 180° C., about 200° C., about 220° C., or about 250° C. The length of time the pressure can be applied can be from a low of about 30 seconds, about 1 minute, about 3 minutes, about 5 minutes, or about 7 minutes to a high of about 10 minutes, about 15 minutes, about 20 minutes, or about 30 minutes, which can depend, at least in part, on the particular product and/or the particular dimensions, e.g., thickness of the product.

Prior to heating the mixture of the lignocellulose substrates and the binder composition, the mixture thereof can be kept, held, or otherwise maintained at a temperature less than about 60° C. for a period of time prior to heating the mixture to a temperature of at least 60° C. The particular temperature of the mixture during the time period before heating can depend, at least in part, on the ambient or environmental temperature where the mixture is located. In one or more embodiments, the mixture can be maintained at a temperature of less than 60° C. without any intentional removal of heat therefrom. In one or more embodiments, the mixture can be maintained at a temperature of less than 60° C. with removal of heat therefrom, e.g., the mixture can be located within a refrigeration device and/or a cooled fluid such as chilled air can be directed toward and/or passed through the mixture. In one or more embodiments, the mixture can be maintained at a temperature of less than 60° C. by controlling or adjusting a water concentration of the mixture. For example, increasing the water concentration of the mixture can reduce, inhibit, or prevent the mixture from undergoing an exothermic reaction.

Prior to heating the mixture to a temperature of at least 60° C., the mixture can be maintained at a temperature less than 60° C., less than 55° C., less than 50° C., less than 45° C., less than 40° C., less than 35° C., or less than 30° C. for at least 10 minutes, at least 13 minutes, at least 15 minutes, at least 17 minutes, at least 20 minutes, at least 23 minutes, at least 25 minutes, at least 27 minutes, at least 30 minutes, at least 33 minutes, at least 35 minutes, at least 37 minutes, at least 40 minutes, at least 43 minutes, at least 45 minutes, at least 47 minutes, at least 50 minutes, at least 53 minutes, at least 55 minutes, at least 57 minutes, or at least 60 minutes. For example, the mixture can be maintained at a temperature less than 60° C. for at least 10 minutes to about 30 minutes, at least about 15 minutes to about 35 minutes, at least about 20 minutes to about 40 minutes, at least about 18 minutes to about 45 minutes, or at least about 15 minutes to about 40 minutes prior to heating the mixture to a temperature of at least 60° C. In another example, the mixture can be maintained at a temperature less than 60° C. for at least 10 minutes, about 30 minutes, about 45 minutes, about 1 hour, about 2 hours, about 3 hours, about 5 hours, about 12 hours, about 18 hours, about 24 hours, or about 30 hours prior to heating the mixture to a temperature of at least 60° C.

Prior to heating the mixture to a temperature of at least 60° C., the amount of energy generated from the mixture due to exothermic reaction(s) between the components of the mixture can be less than about 20 cal/g of the mixture, less than about 18 cal/g of the mixture, less than about 16 cal/g of the mixture, less than about 15 cal/g of the mixture, less than about 14 cal/g of the mixture, or less than about 13.8 cal/g of the mixture. For example, prior to heating the mixture to a temperature of at least 60° C., the amount of energy generated from the mixture due to exothermic reaction(s) between the components of the mixture can be less than 14 cal/g, less than 13.5 cal/g, less than 13 cal/g, less than 12.5 cal/g, less than 12 cal/g, less than 11.5 cal/g, less than 11 cal/g, less than 10.5 cal/g, less than 10 cal/g, less than 9.5 cal/g, less than 9 cal/g, less than 8.5 cal/g, less than 8 cal/g, less than 7.5 cal/g, less than 7 cal/g, less than 6.5 cal/g, less than 6 cal/g, less than 5.5 cal/g, less than 5 cal/g, less than 4.5 cal/g, less than 4 cal/g, less than 3.5 cal/g, less than 3 cal/g, less than 2.5 cal/g. less than 2 cal/g, less than 1.5 cal/g, less than 1 cal/g, or less than 0.5 cal/g of the mixture.

For composite lignocellulose containing products the amount of the binder composition mixed, blended, or otherwise contacted with the lignocellulose material can be from a low of about 0.5 wt %, about 1 wt %, about 2 wt %, about 3 wt %, about 4 wt %, about 5 wt % or about 6 wt % to a high of about 10 wt %, about 12 wt %, about 15 wt %, or about 20 wt %, based on a dry weight of the lignocellulose substrates. For example, a wood composite product can contain from about 1 wt % to about 15 wt %, about 5 wt % to about 15 wt %, about 8 wt % to about 14 wt %, about 10 wt % to about 12 wt %, or about 7 wt % to about 10 wt % binder composition, based on a dry weight of the lignocellulose substrates.

Composite lignocellulose products such as particleboard, fiberboard, plywood, and oriented strand board, can have a thickness from a low of about 1.5 mm, about 5 mm, or about 10 mm to a high of about 30 mm, about 50 mm, or about 100 mm. Wood based or wood containing products can be formed into sheets or boards. The sheets or boards can have a length of about 1.2 m, about 1.8 m, about 2.4 m, about 3 m, or about 3.6 m. The sheets or boards can have a width of about 0.6 m, about 1.2 m, about 1.8 m, about 2.4 m, or about 3 m.

Depending, at least in part, on the number of double bonds per one polyphenol molecule, e.g., the lignin, tannin, and/or novolac resin molecules, the binder compositions could be used for applications other than making lignocellulose composite products. For example, an additional application could be in linear copolymers (the polyphenol can be a pendant group). In another example, an additional application could be in crosslinked copolymer synthesis.

The binder compositions discussed and described above can be combined with one or more additional or second binder compositions to produce a binder or adhesive system (multi-binder system). The one or more second binder compositions or adhesives can be different from the one or more binder compositions discussed and described above. For example the second binder or adhesive composition can be free from at least one of the unsaturated monomers, lignin, tannin, novolac resin, modified phenol formaldehyde resin, bis-phenol A, and/or humic acid.

Illustrative additional or second binder compositions can include, but are not limited to, aldehyde containing or aldehyde based resins; a mixture of Maillard reactants; a reaction product of Maillard reactants; a copolymer of one or more vinyl aromatic derived units and at least one of maleic anhydride and maleic acid; a polyamide-epichlorhydrin polymer; an adduct or polymer of styrene, at least one of maleic anhydride and maleic acid, and at least one of an acrylic acid and an acrylate; a polyacrylic acid based binder; polyvinyl acetate; polymeric methylene diisocyanate ("pMDI"); polyfurfuryl alcohol; or any combination thereof.

Illustrative aldehyde based resins can include, but are not limited to, one or more amino-aldehyde resins, phenol-aldehyde resins, dihydroxybenzene or "resorcinol"-aldehyde resins, or any combination thereof. The amino component of the amino-aldehyde resins can be or include, but is not limited to, urea, melamine, or a combination thereof. The aldehyde based resins can include, but are not limited to, urea-formaldehyde ("UF") resins, phenol-formaldehyde ("PF") resins, melamine-formaldehyde ("MF") resins, resorcinol-formaldehyde ("RF") resins, styrene-acrylic acid; acrylic acid maleic acid copolymer, or any combination thereof. Combinations of amino-aldehyde resins can include, for example, melamine-urea-formaldehyde ("MUF"), phenol-urea-formaldehyde ("PUF") resins, phenol-melamine-formaldehyde ("PMF") resins, phenol-resorcinol-formaldehyde ("PRF") resins, and the like.

Suitable aldehyde compounds for making the amino-aldehyde resins, phenol-aldehyde resins, and/or dihydroxybenzene or "resorcinol"-aldehyde resins can include, but are not limited to, unsubstituted aldehyde compounds and/or substituted aldehyde compounds. For example, suitable aldehyde compounds can be represented by the Formula RCHO, wherein R is hydrogen or a hydrocarbon radical. Illustrative hydrocarbon radicals can include from 1 to about 8 carbon atoms. In another example, suitable aldehyde compounds can also include the so-called masked aldehydes or aldehyde equivalents, such as acetals or hemiacetals. Illustrative aldehyde compounds can include, but are not limited to, formaldehyde, paraformaldehyde, acetaldehyde, propionaldehyde, butyraldehyde, furfuraldehyde, benzaldehyde, or any combination thereof. One or more other aldehydes, such as glyoxal can be used in place of or in combination with formaldehyde and/or other aldehydes. In at least one example, the aldehyde compound can include formaldehyde, UFC, or a combination thereof.

Aldehyde and phenol compounds for making the amino-aldehyde resins, phenol-aldehyde resins, and/or dihydroxybenzene or "resorcinol"-aldehyde resins can be as discussed and described above with reference to the novolac resins.

Suitable urea-formaldehyde resins can be prepared from urea and formaldehyde monomers or from urea-formaldehyde precondensates in manners well known to those skilled in the art. Similarly, melamine-formaldehyde, phenol-formaldehyde, and resorcinol-formaldehyde polymers can be prepared from melamine, phenol, and resorcinol monomers, respectively, and formaldehyde monomers or from melamine-formaldehyde, phenol-formaldehyde, and resorcinol-formaldehyde precondensates. Urea, phenol, melamine, resorcinol, and formaldehyde reactants are commercially available in many forms and any form that can react with the other reactants and does not introduce extraneous moieties deleterious to the desired reaction and reaction product can be used in the preparation of the second copolymer. One suitable class of urea-formaldehyde polymers can be as discussed and described in U.S. Pat. No. 5,362,842.

Similar to formaldehyde and phenol, suitable urea, resorcinol, and melamine are available in many forms. For example, with regard to urea, solid urea, such as prill and urea solutions, typically aqueous solutions, are commonly available. Further, urea may be combined with another moiety, most typically formaldehyde and urea-formaldehyde adducts, often in aqueous solution. Any form of urea or urea in combination with formaldehyde can be used to make a urea-formaldehyde polymer. Both urea prill and combined urea-formaldehyde products are preferred, such as UFC. These types of products can be as discussed and described in U.S. Pat. Nos. 5,362,842 and 5,389,716, for example.

Many suitable urea-formaldehyde polymers are commercially available. Urea-formaldehyde polymers such as the types sold by Georgia-Pacific Chemicals LLC. (e.g., GP®-2928 and GP®-2980) for glass fiber mat applications, those sold by Hexion Specialty Chemicals, and by Arclin Company can be used. Suitable phenol-formaldehyde resins and melamine-formaldehyde resins can include those sold by Georgia Pacific Resins, Inc. (e.g., GP®-2894 and GP®-4878, respectively). These polymers are prepared in accordance with well known methods and contain reactive methylol groups which upon curing form methylene or ether linkages. Such methylol-containing adducts may include N,N'-dimethylol, dihydroxymethylolethylene; N,N'bis(methoxymethyl), N,N'-dimethylolpropylene; 5,5-dimethyl-N,N'dimethylolethylene; N,N'-dimethylolethylene; and the like.

Urea-formaldehyde resins can include from about 45% to about 70%, and preferably, from about 55% to about 65% solids, generally have a viscosity of about 50 cP to about 600 cP, preferably about 150 to about 400 cP, normally exhibit a pH of about 7 to about 9, preferably about 7.5 to about 8.5, and often have a free formaldehyde level of not more than about 3.0%, and a water dilutability of about 1:1 to about 100:1, preferably about 5:1 and above.

Melamine can also be provided in many forms. For example, solid melamine, such as prill and/or melamine solutions can be used. Although melamine is specifically referred to, the melamine can be totally or partially replaced with other aminotriazine compounds. Other suitable aminotriazine compounds can include, but are not limited to, substituted melamines, cycloaliphatic guanamines, or combinations thereof. Substituted melamines include the alkyl melamines and aryl melamines that can be mono-, di-, or tri-substituted. In the alkyl substituted melamines, each alkyl group can contain 1-6 carbon atoms and, preferably 1-4 carbon atoms. Illustrative examples of the alkyl-substituted melamines can include, but are not limited to, monomethyl melamine, dimethyl melamine, trimethyl melamine, monoethyl melamine, and 1-methyl-3-propyl-5-butyl melamine. In the aryl-substituted melamines, each aryl group can contain 1-2 phenyl radicals and, preferably, one phenyl radical. Illustrative examples of aryl-substituted melamines can include, but are not limited to, monophenyl melamine and diphenyl melamine. Any of the cycloaliphatic guanamines can also be used. Suitable cycloaliphatic guanamines can include those having 15 or less carbon atoms. Illustrative cycloaliphatic guanamines can include, but are not limited to, tetrahydrobenzoguanamine, hexahydrobenzoguanamine, 3-methyl-tetrahydrobenzoguanamine, 3-methylhexahydrobenzoguanamine, 3,4-dimethyl-1,2,5,6-tetrahydrobenzoguanamine, and 3,4-dimethylhexahydrobenzoguanamine and mixtures thereof. Mixtures of aminotriazine compounds can include, for example, melamine and an alkyl-substituted melamine, such as dimethyl melamine, or melamine and a cycloaliphatic guanamine, such as tetrahydrobenzoguanamine.

The resorcinol component, if present in the second copolymer, can be provided in a variety of forms. For example, the resorcinol component can be provided as a white/off-white solid or flake and/or the resorcinol component can be heated and supplied as a liquid. Any form of the resorcinol can be used with any form of the aldehyde component to make the resorcinol-aldehyde copolymer. The resorcinol component can be resorcinol itself (i.e., Benzene-1,3-diol). Suitable resorcinol compounds can also be described as substituted phenols. The solids component of a liquid resorcinol-formaldehyde copolymer can be from about 45 wt % to about 75 wt %. Liquid resorcinol-formaldehyde copolymers can have a Brookfield viscosity at 25° C. that varies widely, e.g., from about 200 cP to about 20,000 cP. Liquid resorcinol copolymers typically have a dark amber color.

The mixture of Maillard reactants can include, but is not limited to, a source of a carbohydrate (carbohydrate reactant) and an amine reactant capable of participating in a Maillard reaction with the carbohydrate reactant. In another example, the mixture of Maillard reactants can include a partially pre-reacted mixture of the carbohydrate reactant and the amine reactant. The extent of any pre-reaction can preserve the ability of the mixture of Maillard reactants to be blended with any other components desired to be added into composition such as one or more additives. Suitable Maillard reactants and Maillard reaction products can be as discussed and described in U.S. Patent Application Publication No. 2007/0027283; 2007/0123679; 2007/0123680; 2007/0142596; and 2011/0060095.

The aldehyde based resin(s) and/or the Maillard reactant based binder can be modified by combining with one or more modifiers. The modifier can be or include the copolymer of one or more vinyl aromatic derived units and at least one of maleic anhydride and maleic acid, optionally modified by reaction with one or more base compounds. In another example, the modifier can be or include an adduct of styrene, at least one of maleic anhydride and maleic acid, and at least one of an acrylic acid and an acrylate. In another example, the modifier can be or include the one or more latexes. In another example, the modifier can include two or more of: (1) a copolymer comprising one or more vinyl aromatic derived units and at least one of maleic anhydride and maleic acid; (2) an adduct of styrene, at least one of maleic anhydride and maleic acid, and at least one of an acrylic acid and an acrylate; and (3) one or more latexes. The addition of the one or more modifiers to the aldehyde based binder and/or the Maillard reactant based binder can be as discussed and described in U.S. Patent Application Publication No.: 2011/0060095.

The copolymer of one or more vinyl aromatic derived units and at least one of maleic anhydride and maleic acid can be produced using any suitable reactants. Similarly, the copolymer that includes one or more unsaturated carboxylic acids, one or more unsaturated carboxylic anhydrides, or a combination thereof, one or more vinyl aromatic derived units, and one or more base compounds can be produced using any suitable reactants. Similarly, the copolymer modified by reaction with one or more base compounds, where the copolymer includes one or more unsaturated carboxylic acids, one or more unsaturated carboxylic anhydrides, or a combination thereof, one or more vinyl aromatic derived units, can be produced using any suitable reactants. Illustrative vinyl aromatic derived units can include, but are not limited to, styrene, alpha-methylstyrene, vinyl toluene, and combinations thereof. Preferably, the vinyl aromatic derived units are derived from styrene and/or derivatives thereof. More preferably, the vinyl aromatic derived units are derived from styrene to produce a styrene maleic anhydride (acid) or "SMA" copolymer. Suitable SMA copolymers include resins that contain alternating styrenic and maleic anhydride (acid) monomer units, arranged in random, alternating, and/or block forms. The copolymer that includes one or more unsaturated carboxylic acids, one or more unsaturated carboxylic anhydrides, or a combination thereof, one or more vinyl aromatic derived units, and one or more amines can be as discussed and described in U.S. Patent Application Publication No.: 2011/0165398 and U.S. patent application having Ser. No. 13/228,917.

Polyamide-epichlorhydrin polymers can be made by the reaction of epichlorohydrin and a polyamide under basic conditions (i.e. a pH between about 7 to about 11). The resulting polymer can then be contacted with an acid to stabilize the product. See, e.g., U.S. Pat. Nos. 3,311,594 and 3,442,754. Unreacted epichlorohydrin in the product can be hydrolyzed by the acid to 1,3-dichloro-2-propanol (1,3-DCP), 3-chloro-1,2-propanediol (CPD), and 2,3-dichloro-1-propanol (2,3-DCP). The 1,3-DCP product is the predominant hydrolysis product with CPD being formed in levels of about 10% of the 1,3-DCP and 2,3-DCP being formed in levels of about 1% of the 1,3-DCP. Although the final product can include several other types of organic chlorines (as measured by the difference between inorganic chloride and total chlorine concentrations), the 1,3-DCP and CPD concentrations can be accurately determined by $C^{13}$ NMR and GC-MS measuring techniques known in the art. The 2,3-DCP concentrations are, however, generally below the detection limit of $C^{13}$ NMR so 1,3-DCP and CPD are generally used as measurements for the epichlorohydrin hydrolysis products present in the polymer. Of particular utility are the polyamide-epchlorohydrin polymers, an example of which is sold under the trade names Kymene 557LX and Kymene 557H by Hercules, Inc. and AMRES® from Georgia-Pacific Resins, Inc. These polymers and the process for making the polymers are discussed and described in U.S. Pat. Nos. 3,700,623 and 3,772,076. An extensive description of polymeric-epihalohydrin resins is given in Chapter 2: *Alkaline—Curing Polymeric Amine—Epichlorohydrin* by Espy in *Wet Strength Resins and Their Application* (L. Chan, Editor, 1994).

The adduct or polymer of styrene, at least one of maleic anhydride and maleic acid, and at least one of an acrylic acid and an acrylate can be produced using any suitable reactants. Any suitable acrylic acid or acrylate can be used such as methyl methacrylate, butyl acrylate, methacrylate, or any combination thereof. Preferably, the acrylate is methyl methacrylate (MMA). The adduct can be combined with the aldehyde based polymer, the Maillard reactants, or a combination thereof. In another example, the components of the adduct can be mixed with the aldehyde based polymer, the mixture of Maillard reactants, or a combination thereof.

The adduct can be prepared by dissolving the components of the adduct in a suitable solution. Illustrative solutions can include, but are not limited to, aqueous solutions of sodium hydroxide, ammonium hydroxide, potassium hydroxide, and combinations thereof. The solution can be heated to a temperature of about 70° C. to about 90° C. The solution can be held at the elevated temperature until the components are all at least partially in solution. The solution can then be added to the phenol-aldehyde resin, the mixture of Maillard reactants, or the combination of the phenol-aldehyde resin and the mixture of Maillard reactants.

The adduct can be prepared by combining styrene, at least one of maleic anhydride and maleic acid, and at least one of an acrylic acid and an acrylate to form a terpolymer. The amount of styrene in the adduct can be from a low of about 50 wt %, about 55 wt %, or about 60 wt % to a high of about 75 wt %, about 80 wt %, or about 85 wt %, based on the total weight of the adduct. The amount of the maleic anhydride and/or maleic acid in the adduct can be from a low of about 15 wt %, about 20 wt %, or about 25 wt % to a high of about 40 wt %, about 45 wt %, or about 50 wt %, based on the total weigh of the adduct. The amount of the acrylic acid and/or the acrylate in the adduct can be from a low of about 1 wt %, about 3 wt % or about 5 wt % to a high of about 10 wt %, about 15 wt %, or about 20 wt %, based on the total weight of the adduct.

In another example, the acrylic acid or acrylate can be combined with the copolymer of one or more vinyl aromatic derived units and at least one of maleic anhydride and maleic acid to provide the modifier. For example, combining the acrylic acid or acrylate with SMA can form a styrene maleic anhydride methyl-methacrylate terpolymer. In another example, the modifier can also include a physical mixture of styrene acrylic acid and/or styrene-acrylate copolymer and a SMA copolymer. The adduct or polymer of styrene, at least one of maleic anhydride and maleic acid, and at least one of an acrylic acid and an acrylate and the physical mixture of styrene acrylic acid and/or styrene-acrylate copolymer and a SMA copolymer can be prepared according to the processes discussed and described in U.S. Pat. No. 6,642,299.

The polyacrylic acid based binder can include an aqueous solution of a polycarboxy polymer, a monomeric trihydric alcohol, a catalyst, and a pH adjuster. The polycarboxy polymer can include an organic polymer or oligomer containing more than one pendant carboxy group. The polycarboxy polymer can be a homopolymer or copolymer prepared from unsaturated carboxylic acids including, but not limited to, acrylic acid, methacrylic acid, crotonic acid, isocrotonic acid, maleic acid, cinnamic acid, 2-methylmaleic acid, itaconic acid, 2-methylitaconic acid, $\alpha,\beta$-methyleneglutaric acid, and the like. Other suitable polycarboxy polymers can be prepared from unsaturated anhydrides including, but not limited to, maleic anhydride, itaconic anhydride, acrylic anhydride, methacrylic anhydride, and the like, as well as mixtures thereof.

Illustrative trihydric alcohols can include, but are not limited to, glycerol, trimethylolpropane, trimethylolethane, triethanolamine, 1,2,4-butanetriol, and the like. The one or more trihydric alcohols can be mixed with other polyhydric alcohols. Other polyhydric alcohols can include, but are not limited to, ethylene, glycol, 1,3-propanediol, 1,4-butanediol, 1,6-hexanediol, 2-butene-1, erythritol, pentaerythritol, sorbitol, and the like. The catalyst can include an alkali metal salt of a phosphorous-containing organic acid; particularly alkali metal salts of phosphorous acid, hypophosphorous acid, and polyphosphoric acids. Illustrative catalysts can include, but are not limited to, sodium, sodium phosphite, potassium phosphite, disodium pyrophosphate, tetrasodium pyrophosphate, sodium tripolyphosphate, sodium hexametaphosphate, potassium phosphate, potassium polymetaphosphate, potassium polyphosphate, potassium tripolyphosphate, sodium trimetaphosphate, and sodium tetrametaphosphate, or any combination thereof. Illustrative polyacrylic acid based polymers can be as discussed and described in U.S. Pat. No. 7,026,390.

The binder compositions discussed and described herein can be combined with the one or more second binders or adhesives in any desired amount with respect to one another to produce a binder system. For example, the amount of either the first binder composition or the second binder composition in the binder system can be from about 0.1 wt % to about 99 wt %, based on the combined solids weight of the first and second binder compositions. In another example, the binder system can have a concentration of the first binder composition in an amount from a low of about 0.5 wt %, about 1 wt %, about 2 wt %, about 3 wt %, or about 4 wt % to a high of about 10 wt %, about 20 wt %, about 30 wt %, about 40 wt %, about 50 wt %, about 60 wt %, about 70 wt %, about 80 wt %, or about 90 wt %, based on the combined solids weight of the first and second binder compositions.

The binder composition can be free or essentially free of formaldehyde for use in the production of the composite lignocellulose products, e.g., wood products such as particleboard and plywood. As used herein, the term "essentially free of formaldehyde" means the binder composition does not include or contain any intentionally added formaldehyde or compounds that can decompose, react, or otherwise form formaldehyde. Said another way, the term "essentially free of formaldehyde" means the binder composition does not contain formaldehyde or compounds that can form formaldehyde, but may include formaldehyde present as an impurity. Accordingly, depending on the particular multifunctional aldehyde(s) used to produce the binder compositions discussed and described herein, the binder composition can be referred to as "no added formaldehyde" or "NAF" binder composition.

The binder composition can meet or exceed the formaldehyde emission standards required by the California Air Resources Board ("CARB") Phase 1 (less than 0.1 parts per million "ppm" formaldehyde for particleboard), and Phase 2 (less than 0.09 ppm formaldehyde for particleboard). The binder compositions discussed and described herein can also meet or exceed the formaldehyde emission standards required by the Japanese JIS/JAS F* (does not exceed 0.5 mg/L formaldehyde for particleboard), Japanese JIS/JAS F** (does not exceed 0.3 mg/L formaldehyde for particleboard), European E1, and European E2 standards.

The composite lignocellulose containing products produced with the binder compositions and/or binder systems discussed and described herein can exhibit a low level of formaldehyde emission. A suitable test for determining formaldehyde emission from a composite wood product that includes an at least partially cured binder composition and/or binder system can include ASTM D6007-02 and AST E1333-10. For example, the composite lignocellulose containing products containing an at least partially cured binder composition and/or binder system can exhibit a formaldehyde emission of zero. In another example, the composite lignocellulose containing products containing an at least partially cured binder composition and/or binder system can exhibit a formaldehyde emission of less than about 1 part per million ("ppm"), less than about 0.9 ppm, less than about 0.08 ppm, less than about 0.07 ppm, less than about 0.06 ppm, less than about 0.05 ppm, less than about 0.04 ppm, less than about 0.03 ppm, less than about 0.02 ppm, less than about 0.01 ppm, or less than about 0.005 ppm.

The method for making the composite lignocellulose containing products can include a continuous or semi-continuous blending process in which the lignocellulose substrates and the other components of the mixture, e.g., the binder composition, can be introduced to a blender at a first or introduction region, end, area, or other location(s) configured to receive the components and the mixture can be withdrawn from the blender via one or more mixture recovery outlets. The blender can be configured to contain anywhere from a few hundred kilograms to several thousand kilograms. For example, in a single blender anywhere from a low of about 500 kg/hr, about 5,000 kg/hr, about 10,000 kg/hr, or about 13,000 kg/hr to a high of about 16,000 kg/hr, about 20,000 kg/hr, about 25,000 kg/hr, or about 30,000 kg/hr of the mixture can be recovered from the blender. As the mixture exits the blender, the mixture can be deposited onto a conveyor belt and can be transported to one or more dryers, moistening systems, presses, and/or other processing equipment. For example, in at least one specific embodiment, a particle board product can be made blending a first or "face" mixture and a second or "core" mixture in a first and second blend, respectively. The first blender can produce from about 13,600 kg/hr to about 15,900 kg/hr of a "face" mixture and the second blender can produce from about 18,100 kg/hr to about 20,400 kg/hr of a "core" mixture. The "face" and "core" mixtures can be used to produce a particleboard panel or sheet, where the "face" mixture makes up the outer layers of the particleboard and the "core" mixture makes up the inner or core layer of the particleboard.

Composite products in the shape or form of a panel, sheet, board, or the like can be in the form of a rectangular prism that includes six outer surfaces, i.e., three pairs of oppositely facing surfaces. The first pair of oppositely facing surfaces of the composite product can include a first or "top" surface and an opposing second or "bottom" surface. The second and third pairs of oppositely facing surfaces of the composite product can be referred to as the "side surfaces" that have a surface area less than the surface area of the first and second surfaces. As such, composite products in the shape or form of a panel, sheet, board, or the like can have an average thickness, where the average thickness is the length or distance between the first and second surfaces.

If the composite product is in the form of a panel, sheet, board, or the like, the amount or length of time the mixture can be heated can range from a low of about 5 seconds per millimeter (s/mm), about 10 s/mm, about 12 s/mm, or about 15 s/mm to a high of about 17 s/mm, about 19 s/mm, about 21 s/mm, about 23 s/mm, about 25 s/mm, about 27 s/mm, about 30 s/mm, about 35 s/mm, about 40 s/mm, about 50 s/mm, or about 60 s/mm, where the length refers to the average thickness of the composite product. For example, the mixture can be heated for a time of about 7 s/mm to about 27 s/mm, about 9 s/mm to about 24 s/mm, about 11 s/mm to about 22 s/mm, about 8 s/mm to about 20 s/mm, about 14 s/mm to about 18 s/mm, about 6 s/mm to about 14 s/mm, about 10 s/mm to about 18 s/mm, or about 10 s/mm to about 16 s/mm, where the length refers to the average thickness of the composite product. In another example, the mixture can be heated for a time less than 22 s/mm, less than 20 s/mm, less than 18 s/mm, less than 17 s/mm, less than 16 s/mm, less than 15 s/mm, less than 14 s/mm, less than 13 s/mm, or less than 12 s/mm, where the length refers to the average thickness of the composite product. In one specific example, a composite product in the form of a panel, sheet, board, or the like and having an average thickness of about 15 mm and subjected to a total heating time of about 4 minutes would correspond to heating the mixture for about 16 s/mm. In at least one specific example, the mixture can be heated to a temperature of about 160° C. to about 170° C. for a time of 13 s/mm to about 19 s/mm.

The composite product can have a density from a low of about 0.5 g/cm$^3$, about 0.55 g/cm$^3$, about 0.6 g/cm$^3$, about 0.63 g/cm$^3$, about 0.65 g/cm$^3$, about 0.67 g/cm$^3$, or about 0.7 g/cm$^3$ to a high of about 0.75 g/cm$^3$, about 0.77 g/cm$^3$, about 0.8 g/cm$^3$, about 0.83 g/cm$^3$, about 0.85 g/cm$^3$, about 0.88 g/cm$^3$, about 0.93 g/cm$^3$, about 0.97 g/cm$^3$, or about 1 g/cm$^3$. For example, the composite product can have a density of about 0.7 g/cm$^3$ to about 0.75 g/cm$^3$, about 0.65 g/cm$^3$ to about 0.85 g/cm$^3$, about 0.65 g/cm$^3$ to about 0.8 g/cm$^3$, about 0.67 g/cm$^3$ to about 0.77 g/cm$^3$, about 0.5 g/cm$^3$, to about 1 g/cm$^3$, about 0.5 g/cm$^3$, to about 0.8 g/cm$^3$, about 0.5 g/cm$^3$ to about 0.75 g/cm$^3$, or about 0.64 g/cm$^3$ to about 0.8 g/cm$^3$. In one or more embodiments, the composite product can have density less than 1 g/cm$^3$, less than 0.95 g/cm$^3$, less than 0.88 g/cm$^3$, less than 0.85 g/cm$^3$, less than 0.83 g/cm$^3$, less than 0.8 g/cm$^3$, less than 0.79 g/cm$^3$, less than 0.78 g/cm$^3$, less than 0.77 g/cm$^3$, less than 0.76 g/cm$^3$, less than 0.75 g/cm$^3$, less than 0.74 g/cm$^3$, or less than 0.73 g/cm$^3$.

The composite product can have an internal bond strength from a low of about 0.3 MPa, about 0.32 MPa, about 0.34 MPa, about 0.35 MPa, about 0.37 MPa, about 0.4 MPa, about 0.42 MPa, about 0.48 MPa, about 0.52 MPa, about 0.55 MPa, or about 0.58 MPa to a high of about 0.69 MPa, about 0.75 MPa, about 0.83 MPa, about 0.9 MPa, about 0.97 MPa, about 1.05 MPa, about 1.15 MPa, about 1.2 MPa, about 1.25 MPa, about 1.3 MPa, about 1.35 MPa, about 1.4 MPa, about 1.45 MPa, about 1.5 MPa, about 1.55 MPa, about 1.6 MPa, or about 1.7 MPa. For example, the composite product can have an internal bond strength of about 0.35 MPa to about 0.55 MPa, about 0.4 MPa to about 0.6 MPa, about 0.48 MPa to about 0.69 MPa, about 0.59 MPa to about 0.86 MPa, about 0.55 MPa to about 0.9 MPa, or about 0.51 MPa to about 0.85 MPa. In one or more embodiments, the composite product can have an internal bond strength of at least 0.33 MPa, at least 0.32 MPa, at least 0.34 MPa, at least 0.38 MPa, at least 0.41 MPa, at least 0.45 MPa, at least 0.48 MPa, at least 0.51 MPa, at least 0.55 MPa, at least 0.58 MPa, at least 0.62 MPa, at least 0.66 MPa, at least 0.69 MPa, at least 0.72 MPa, at least 0.76 MPa, or at least 0.79 MPa. The internal bond strength can be determined according to the test procedure provided for in ASTM D1037-06a.

In one or more embodiments, the composite product can have a density less than 1 g/cm$^3$, less than 0.95 g/cm$^3$, less than 0.9 g/cm$^3$, less than 0.85 g/cm$^3$, less than 0.8 g/cm$^3$, less than 0.79 g/cm$^3$, less than 0.78 g/cm$^3$, less than 0.77 g/cm$^3$, less than 0.76 g/cm$^3$, less than 0.75 g/cm$^3$, less than 0.74 g/cm$^3$, or less than 0.73 g/cm$^3$ and an internal bond strength of at least 0.3 MPa, at least 0.35 MPa, at least 0.4 MPa, at least 0.48 MPa, at least 0.51 MPa, at least 0.55 MPa, at least 0.58 MPa, at least 0.62 MPa, at least 0.65 MPa, or at least 0.69 MPa. In at least one specific example, the composite product can have a density less than 0.8 g/cm$^3$ and internal bond strength of at least 0.48 MPa. In at least one other specific example, the composite product can have a density less than 0.8 g/cm$^3$ and internal bond strength of at least 0.69 MPa. In at least one other specific example, the composite product can have a density of less than 0.73 g/cm$^3$ and internal bond strength of at least 0.48 MPa. In still another example, the composite product can have a density of less than 0.73 g/cm$^3$ and internal bond strength of at least 0.58 MPa.

Referring to particleboard in particular, particleboard made according to one or more embodiments discussed and described herein can meet or exceed the requirements for H-1, H-2, H-3, M-0, M-1, M-S, M-2, M-3i, LD-1, and/or LD-2 grade particleboard as described in the American National Standards Institute (ANSI) for particleboard, i.e., ANSI A208.1-2009 Particleboard, approved Feb. 2, 2009. Particleboard made according to one or more embodiments discussed and described herein can meet or exceed the requirements for PBU, D-2, D-3, and/or M-3 as defined by the ANSI for particleboard, i.e., ANSI A208.1-2009 Particleboard, approved Feb. 2, 2009. For example, Tables A and B set out certain requirements for the different grades of particleboard. Referring to oriented strand board (OSB) in particular, OSB made according to one or more embodiments discussed and described herein can meet or exceed the U.S. Department of Commerce Voluntary Performance Standard PS 2. Referring to plywood in particular, plywood made according to one or more embodiments discussed and described herein can meet or exceed the U.S. Department of Commerce Voluntary Performance Standard PS 1 and/or PS-2.

Embodiments of the present disclosure further relate to any one or more of the following paragraphs:

1. A binder composition, comprising: an unsaturated monomer; and at least one of: a lignin, a tannin, a novolac resin, a modified phenol formaldehyde resin, bis-phenol A, and humic acid.

2. A method for preparing a composite product, comprising: contacting a plurality of lignocellulose substrates with a binder composition, wherein the binder composition comprises: an unsaturated monomer; and at least one of: a lignin, a tannin, a novolac resin, a modified phenol formaldehyde resin, bis-phenol A, and humic acid; and at least partially curing the binder composition to produce a composite lignocellulose-containing product.

3. A composite product, comprising: a plurality of lignocellulose substrates and an at least partially cured binder composition, wherein the binder composition, prior to at least partially curing, comprises: an unsaturated monomer; at least one of: a lignin, a tannin, a novolac resin, a modified phenol formaldehyde resin, bis-phenol A, and humic acid.

4. The binder composition, method, and/or composite product according to any one of paragraphs 1 to 3, wherein prior to at least partially curing the binder composition the unsaturated monomer and the at least one of the lignin, tannin, novolac resin, modified phenol formaldehyde resin, bis-phenol A, and humic acid are at least partially reacted with one another.

5. The method and/or composite product according to any one of paragraphs 1 to 4, wherein an amount of the binder composition contacted with the lignocellulose substrates ranges from about 3 wt % to about 20 wt %, based on a dry weight of the lignocellulose substrates.

6. The method and/or composite product according to any one of paragraphs 1 to 5, wherein the lignocellulose substrates are at least partially oxidized in the presence of an oxidant prior to contacting with the binder composition.

7. The method and/or composite product according to paragraph 6, wherein the oxidant comprises one or more inorganic peroxy compounds, one or more organic peroxy compounds, or a combination thereof.

8. The method and/or composite product according to paragraph 6 or 7, wherein the oxidant is hydrogen peroxide.

9. The method and/or composite product according to any one of paragraphs 6 to 8, wherein the oxidant is present in an amount from about 20 wt % to about 100 wt %, based on a dry weight of the lignocellulose substrates.

10. The method and/or composite product according to any one of paragraphs 1 to 9, wherein the lignocellulose substrates are at least partially oxidized in the presence of an oxidant and a catalyst.

11. The method and/or composite product according to paragraph 10, wherein the catalyst comprises one or more metal ions of iron, copper, manganese, tungsten, molybdenum, or any combination thereof; one or more tertiary amines; or a combination thereof.

12. The method and/or composite product according to paragraph 10 or 11, wherein the catalyst comprises a metal ion, a tertiary amine, a phosphate, a bisulfite, a metabisulfite, hydroxymethanesulfonic acid monosodium salt, a metal salt, tetraacetylethylenediamine, cyanamide, or any combination thereof.

13. The method and/or composite product according to any one of paragraphs 1 to 12, wherein the lignocellulose substrates are at least partially oxidized in the presence of an oxidant after contacting with the binder composition.

14. The method and/or composite product according to any one of paragraphs 1 to 13, wherein at least partially curing the binder composition comprises heating the lignocellulose substrates contacted with the binder composition to a temperature from about 100° C. to about 250° C.; and pressing the lignocellulose substrates to a pressure from about 1 MPa to about 6 MPa.

15. The method and/or composite product according to any one of paragraphs 1 to 14, wherein the composite lignocellulose-containing product comprises a particleboard, a fiberboard, a plywood, an oriented strand board, a laminated veneer lumber, or a laminated veneer board.

16. The binder composition, method, and/or composite product according to any one of paragraphs 1 to 15, wherein the unsaturated monomer is nonionic.

17. The binder composition, method, and/or composite product according to any one of paragraphs 1 to 16, wherein the unsaturated monomer comprises an unsaturated glycidyl ether, an unsaturated glycidyl ester, an unsaturated monoepoxide, an unsaturated methylol compound, maleic anhydride, or any combination thereof.

18. The binder composition, method, and/or composite product according to any one of paragraphs 1 to 17, wherein the unsaturated monomer and the at least one of the lignin, tannin, novolac resin, modified phenol formaldehyde resin, bis-phenol A, and humic acid are at least partially reacted with one another.

19. The binder composition, method, and/or composite product according to any one of paragraphs 1 to 18, wherein the unsaturated monomer and the at least one of the lignin, tannin, novolac resin, modified phenol formaldehyde resin, bis-phenol A, and humic acid are at least partially reacted with one another at a temperature from about 25° C. to about 100° C. and a pressure from about 50 kPa to about 1,000 kPa.

20. The binder composition, method, and/or composite product according to any one of paragraphs 1 to 19, wherein the at least one of the lignin, tannin, novolac resin, modified phenol formaldehyde resin, bis-phenol A, and humic acid is combined with a liquid medium.

21. The binder composition, method, and/or composite product according to any one of paragraphs 1 to 20, wherein the liquid medium comprises water.

22. The binder composition, method, and/or composite product according to paragraph 21, wherein the binder composition has a water concentration from about 40 wt % to about 70 wt %, based on a solids weight of the at least one of the lignin, tannin, novolac resin, modified phenol formaldehyde resin, bis-phenol A, and humic acid.

23. The binder composition, method, and/or composite product according to any one of paragraphs 1 to 22, wherein the binder composition has a viscosity from about 100 cP to about 10,000 cP at a temperature of 25° C.

24. The binder composition, method, and/or composite product according to any one of paragraphs 1 to 23, wherein the unsaturated monomer comprises an unsaturated glycidyl ether.

25. The binder composition, method, and/or composite product according to paragraph 24, wherein the unsaturated glycidyl ether comprises vinyl glycidyl ether, isopropenyl glycidyl ether, oleyl glycidyl ether, allyl glycidyl ether, p-vinylbenzyl glycidyl ether, o-allyl phenyl glycidyl ether, butenyl glycidyl ether, 4-vinylcyclohexyl glycidyl ether, abietylglycidyl ether, cyclohexeneylmethyl glycidyl ether, methallyl glycidyl ether, or any combination thereof.

26. The binder composition, method, and/or composite product according to any one of paragraphs 1 to 25, wherein the unsaturated monomer comprises an unsaturated glycidyl ester.

27. The binder composition, method, and/or composite product according to paragraph 26, wherein the unsaturated glycidyl ester comprises glycidyl methacrylate, glycidyl acrylate, glycidyl crotonate, glycidyl oleate, di-glycidyl maleate, di-glycidyl fumarate, or any combination thereof.

28. The binder composition, method, and/or composite product according to any one of paragraphs 1 to 27, wherein the unsaturated monomer comprises an unsaturated monoepoxide.

29. The binder composition, method, and/or composite product according to paragraphs 28, wherein the unsaturated mono-epoxide comprises 4-vinyl cyclohexene oxide, 1-methyl-4-isopropenyl cyclohexene monoxide, butadiene monoxide, or any combination thereof.

30. The binder composition, method, and/or composite product according to any one of paragraphs 1 to 29, wherein the unsaturated monomer comprises an unsaturated methylol compound.

31. The binder composition, method, and/or composite product according to paragraph 30, wherein the unsaturated methylol compound comprises N-methylol acrylamide, N-methylol methacrylamide, N-methylol crotonamide, or any combination thereof.

32. The binder composition, method, and/or composite product according to any one of paragraphs 1 to 31, wherein the tannin is present, and wherein the tannin is extracted from one or more trees belonging to the genera selected from the group consisting of: *Castanea sativa, Terminalia, Phyllantus, Caesalpina coriaria, Caesalpinia spinosa, Acacia mearnsii, Schinopsis, Tsuga, Rhus, Juglans, Carya illinoinensis, Juglans, Carya illinoinensis,* and *Pinus*.

33. The binder composition, method, and/or composite product according to any one of paragraphs 1 to 32, wherein the lignin is present, and wherein the lignin is extracted from one or more trees selected from the group consisting of: alder, ash, aspen, basswood, beech, birch, cedar, cherry, cottonwood, cypress, elm, fir, gum, hackberry, hickory, maple, oak, pecan, pine, poplar, redwood, sassafras, spruce, sycamore, walnut, and willow.

34. The binder composition, method, and/or composite product according to any one of paragraphs 1 to 33, wherein the binder composition is essentially free of formaldehyde.

35. The binder composition, method, and/or composite product according to any one of paragraphs 1 to 34, wherein the binder composition is free of formaldehyde.

36. The binder composition, method, and/or composite product according to any one of paragraphs 1 to 35, wherein the unsaturated monomer is present in an amount from about 0.1 wt % to about 10 wt %, based on the total solids weight of the at least one of the lignin, tannin, novolac resin, modified phenol formaldehyde resin, bis-phenol A, and humic acid.

37. The binder composition, method, and/or composite product according to any one of paragraphs 1 to 36, wherein the lignin and tannin are present and the binder composition is free from the novolac resin.

38. The binder composition, method, and/or composite product according to any one of paragraphs 1 to 37, wherein the binder composition further comprises an aldehyde based resin; a mixture of Maillard reactants; a reaction product of Maillard reactants; a copolymer of one or more vinyl aromatic derived units and at least one of maleic anhydride and maleic acid; a polyamide-epichlorhydrin polymer; an adduct or polymer of styrene, at least one of maleic anhydride and maleic acid, and at least one of an acrylic acid and an acrylate; a polyacrylic acid based binder; polyvinyl acetate; polymeric methylene diisocyanate; polyfurfuryl alcohol; or any combination thereof.

39. A composite product, comprising: an at least partially cured composition having a density less than 1 g/cm$^3$ and an internal bond strength of at least 0.35 MPa, wherein the composition, prior to curing, comprises a plurality of lignocellulose substrates, an unsaturated monomer and at least one of: a lignin, a tannin, a novolac resin, a modified phenol formaldehyde resin, bis-phenol A, and humic acid.

40. A composite product comprising a mixture that has been heated to a temperature from about 60° C. to about 300° C., wherein the mixture, prior to being heated, comprises a plurality of lignocellulose substrates, an unsaturated monomer and at least one of: a lignin, a tannin, a novolac resin, a modified phenol formaldehyde resin, bis-phenol A, and humic acid, and wherein the heated mixture has an internal bond strength of at least 0.35 MPa and a density less than 1 g/cm$^3$.

41. A composite product, comprising: an at least partially cured composition, wherein the at least partially composition, prior to curing, comprises a plurality of lignocellulose substrates, an unsaturated monomer and at least one of: a lignin, a tannin, a novolac resin, a modified phenol formaldehyde resin, bis-phenol A, and humic acid.

42. A composite product comprising a mixture that has been heated to a temperature from about 60° C. to about 300° C., and wherein prior to heating the mixture comprises a plurality of lignocellulose substrates, an unsaturated monomer and at least one of: a lignin, a tannin, a novolac resin, a modified phenol formaldehyde resin, bis-phenol A, and humic acid.

43. The composite product according to paragraph 42, wherein the unsaturated monomer is reacted with the at least one of the lignin, the tannin, the novolac resin, the modified phenol formaldehyde resin, bis-phenol A, and humic acid.

44. The binder composition, method, and/or composite product according to any one of paragraphs 1 to 38, wherein the unsaturated monomer comprises maleic anhydride.

45. A binder composition, comprising: at least one unsaturated monomer; and at least one polyphenolic compound comprising a lignin, a tannin, a novolac resin, a modified phenol formaldehyde resin, bis-phenol A, humic acid, or any mixture thereof.

46. A method for preparing a composite product, comprising: contacting a plurality of lignocellulose substrates with a binder composition, wherein the binder composition comprises: at least one unsaturated monomer; and at least one polyphenolic compound comprising a lignin, a tannin, a novolac resin, a modified phenol formaldehyde resin, bisphenol A, humic acid, or any mixture thereof; and at least partially curing the binder composition to produce a composite lignocellulose-containing product.

47. A composite product, comprising: a plurality of lignocellulose substrates and an at least partially cured binder composition, wherein the binder composition, prior to at least partially curing, comprises: at least one unsaturated monomer; and at least one polyphenolic compound comprising a lignin, a tannin, a novolac resin, a modified phenol formaldehyde resin, bis-phenol A, humic acid, or any mixture thereof.

48. The binder composition, method, and/or composite product according to any one of paragraphs 45 to 47, wherein the unsaturated monomer is nonionic.

49. The binder composition, method, and/or composite product according to any one of paragraphs 45 to 48, wherein the unsaturated monomer comprises an unsaturated glycidyl ether, an unsaturated glycidyl ester, an unsaturated mono-epoxide, an unsaturated methylol compound, maleic anhydride, or any mixture thereof.

50. The binder composition, method, and/or composite product according to any one of paragraphs 45 to 49, wherein the unsaturated monomer and the polyphenolic compound are at least partially reacted with one another.

51. The binder composition, method, and/or composite product according to any one of paragraphs 45 to 50, wherein the unsaturated monomer does not contain an aromatic ring.

52. The binder composition, method, and/or composite product according to any one of paragraphs 45 to 51, wherein the binder composition further comprises water in an amount of about 40 wt % to about 70 wt %, based on a solids weight of the polyphenolic compound, and wherein the binder composition comprises the unsaturated monomer in an amount of about 0.1 wt % to about 50 wt %, based on the solids weight of the polyphenolic compound.

53. The binder composition, method, and/or composite product according to any one of paragraphs 45 to 52, wherein the unsaturated monomer comprises an unsaturated glycidyl ether, and wherein the unsaturated glycidyl ether comprises vinyl glycidyl ether, isopropenyl glycidyl ether, oleyl glycidyl ether, allyl glycidyl ether, p-vinylbenzyl glycidyl ether, o-allyl phenyl glycidyl ether, butenyl glycidyl ether, 4-vinylcyclohexyl glycidyl ether, abietylglycidyl ether, cyclohexeneylmethyl glycidyl ether, methallyl glycidyl ether, or any mixture thereof.

54. The binder composition, method, and/or composite product according to any one of paragraphs 45 to 53, wherein the unsaturated monomer comprises an unsaturated glycidyl ester, and wherein the unsaturated glycidyl ester comprises glycidyl methacrylate, glycidyl acrylate, glycidyl crotonate, glycidyl oleate, di-glycidyl maleate, di-glycidyl fumarate, or any mixture thereof.

55. The binder composition, method, and/or composite product according to any one of paragraphs 45 to 54, wherein the unsaturated monomer comprises an unsaturated mono-epoxide, and wherein the unsaturated mono-epoxide comprises 4-vinyl cyclohexene oxide, 1-methyl-4-isopropenyl cyclohexene monoxide, butadiene monoxide, or any mixture thereof.

56. The binder composition, method, and/or composite product according to any one of paragraphs 45 to 55, wherein the unsaturated monomer comprises an unsaturated methylol compound, and wherein the unsaturated methylol compound comprises N-methylol acrylamide, N-methylol methacrylamide, N-methylol crotonamide, or any mixture thereof.

57. The binder composition, method, and/or composite product according to any one of paragraphs 45 to 56, wherein the unsaturated monomer comprises maleic anhydride.

58. The binder composition, method, and/or composite product according to any one of paragraphs 45 to 57, wherein the polyphenolic compound comprises the tannin, and wherein the tannin is extracted from one or more trees belonging to the genera selected from the group consisting of: *Castanea sativa, Terminalia, Phyllantus, Caesalpina coriaria, Caesalpinia spinosa, Acacia mearnsii, Schinopsis, Tsuga, Rhus, Juglans, Carya illinoinensis, Juglans, Carya illinoinensis*, and *Pinus*.

59. The binder composition, method, and/or composite product according to any one of paragraphs 45 to 58, wherein the polyphenolic compound comprises the lignin, and wherein the lignin is extracted from one or more trees selected from the group consisting of: alder, ash, aspen, basswood, beech, birch, cedar, cherry, cottonwood, cypress, elm, fir, gum, hackberry, hickory, maple, oak, pecan, pine, poplar, redwood, sassafras, spruce, sycamore, walnut, and willow.

60. The binder composition, method, and/or composite product according to any one of paragraphs 45 to 59, wherein the polyphenolic compound comprises the lignin, the tannin, bis-phenol A, humic acid, or any mixture thereof, and wherein the binder composition is free of formaldehyde.

61. The binder composition, method, and/or composite product according to any one of paragraphs 45 to 60, wherein the binder composition further comprises an aldehyde based resin; a mixture of Maillard reactants; a reaction product of Maillard reactants; a copolymer of one or more vinyl aromatic derived units and at least one of maleic anhydride and maleic acid; a polyamide-epichlorhydrin polymer; an adduct or polymer of styrene, at least one of maleic anhydride and maleic acid, and at least one of an acrylic acid and an acrylate; a polyacrylic acid based binder; polyvinyl acetate; polymeric methylene diisocyanate; polyfurfuryl alcohol; or any combination thereof.

62. The method according to any one of paragraphs 46 to 61, wherein an amount of the binder composition contacted with the lignocellulose substrates ranges from about 3 wt % to about 20 wt %, based on a dry weight of the lignocellulose substrates.

63. The method according to any one of paragraphs 46 to 62, wherein the lignocellulose substrates are at least partially oxidized in the presence of an oxidant prior to contacting with the binder composition.

64. The method according to any one of paragraphs 46 to 63, wherein the oxidant comprises one or more inorganic peroxy compounds, one or more organic peroxy compounds, or a combination thereof.

65. The method according to any one of paragraphs 46 to 64, wherein the oxidant is hydrogen peroxide.

66. The method according to any one of paragraphs 46 to 64, wherein the binder composition further comprises water in an amount of about 40 wt % to about 70 wt %, based on a solids weight of the polyphenolic compound, wherein the binder composition comprises the unsaturated monomer in an amount of about 0.1 wt % to about 50 wt %, based on the solids weight of the polyphenolic compound, and wherein the oxidant is present in an amount from about 20 wt % to about 100 wt %, based on a dry weight of the lignocellulose substrates.

67. The method according to any one of paragraphs 46 to 66, wherein the lignocellulose substrates are at least partially oxidized in the presence of an oxidant and a catalyst.

68. The method according to paragraph 67, wherein the catalyst comprises one or more metal ions of iron, copper, manganese, tungsten, molybdenum, or any combination thereof; one or more tertiary amines; or a combination thereof.

69. The method according to paragraph 67, wherein the catalyst comprises a metal ion, a tertiary amine, a phosphate, a bisulfite, a metabisulfite, hydroxymethanesulfonic acid monosodium salt, a metal salt, tetraacetylethylenediamine, cyanamide, or any combination thereof.

70. The method according to any one of paragraphs 46 to 69, wherein the lignocellulose substrates are at least partially oxidized in the presence of an oxidant after contacting with the binder composition.

71. The method according to any one of paragraphs 46 to 70, wherein at least partially curing the binder composition comprises heating the lignocellulose substrates contacted with the binder composition to a temperature from about 100° C. to about 250° C.; and pressing the lignocellulose substrates to a pressure from about 1 MPa to about 6 MPa.

72. The method according to any one of paragraphs 46 to 71, wherein the composite lignocellulose-containing product comprises a particleboard, a fiberboard, a plywood, an oriented strand board, a laminated veneer lumber, or a laminated veneer board.

73. The binder composition, method, and/or composite product according to any one of paragraphs 45 to 72, wherein the binder composition further comprises water in an amount from a low of about 1 wt %, about 5 wt %, about 10 wt %, about 15 wt %, about 20 wt %, about 25 wt %, about 30 wt %, about 35 wt %, or about 40 wt % to a high of about 50 wt %, about 55 wt %, about 60 wt %, about 65 wt %, or about 70 wt %, based on a solids weight of the polyphenolic compound, and wherein the binder composition comprises the unsaturated monomer in an amount from a low of about 0.1 wt %, about 1 wt %, about 3 wt %, about 5 wt %, about 7 wt %, about 10 wt %, about 12 wt %, or about 15 wt % to a high of about 25 wt %, about 30 wt %, about 35 wt %, about 40 wt %, about 45 wt %, or about 50 wt %, based on the solids weight of the polyphenolic compound.

74. The binder composition, method, and/or composite product according to any one of paragraphs 45 to 73, wherein the unsaturated monomer and the polyphenolic compound are at least partially reacted with one another, and wherein the binder composition comprises at least two unsaturated monomers.

75. The binder composition, method, and/or composite product according to any one of paragraphs 45 to 74, wherein the unsaturated monomer and the polyphenolic compound are at least partially reacted with one another, wherein the binder composition comprises at least two unsaturated monomers, and wherein the at least two unsaturated monomers comprise an unsaturated glycidyl ether and an unsaturated glycidyl ester, an unsaturated glycidyl ether and an unsaturated mono-epoxide, an unsaturated glycidyl ether and an unsaturated methylol compound, an unsaturated glycidyl ether and maleic anhydride, an unsaturated glycidyl ester and an unsaturated mono-epoxide, an unsaturated glycidyl ester and an unsaturated methylol compound, an unsaturated glycidyl ester and maleic anhydride, an unsaturated mono-epoxide and an unsaturated methylol compound, or an unsaturated glycidyl ester and maleic anhydride.

76. The binder composition, method, and/or composite product according to any one of paragraphs 45 to 75, wherein the unsaturated monomer comprises an unsaturated glycidyl ether, an unsaturated glycidyl ester, an unsaturated mono-epoxide, an unsaturated methylol compound, or any mixture thereof.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A binder composition, comprising a reaction product of an unsaturated monomer and at least two polyphenolic compounds selected from the group consisting of: a tannin, a lignin, a novolac resin, a modified phenol formaldehyde resin, bis-phenol A, and humic acid, wherein the binder composition comprises about 0.05 wt % to 10 wt % of the unsaturated monomer, based on a solids weight of the at least two polyphenolic compounds.

2. The binder composition of claim 1, wherein the binder composition further comprises water in an amount of about 40 wt % to about 70 wt %, based on a solids weight of the at least two polyphenolic compounds.

3. The binder composition of claim 1, wherein the unsaturated monomer comprises an unsaturated glycidyl ether.

4. The binder composition of claim 1, wherein the unsaturated monomer comprises an unsaturated glycidyl ester.

5. The binder composition of claim 1, wherein the unsaturated monomer comprises an unsaturated mono-epoxide.

6. The binder composition of claim 1, wherein the unsaturated monomer comprises an unsaturated methylol compound.

7. The binder composition of claim 1, wherein the unsaturated monomer comprises maleic anhydride.

8. The binder composition of claim 1, wherein the unsaturated monomer comprises at least two compounds selected from the group consisting of: an unsaturated glycidyl ether, an unsaturated glycidyl ester, an unsaturated mono-epoxide, an unsaturated methylol compound, and maleic anhydride.

9. The binder composition of claim 1, wherein the at least two polyphenolic compounds are selected from the group consisting of: a tannin, a lignin, a novolac resin, bis-phenol A, and humic acid.

10. The binder composition of claim 1, wherein the at least two polyphenolic compounds comprise a tannin and a lignin.

11. The binder composition of claim 1, wherein the binder composition comprises about 0.05 wt % to about 8.5 wt % of the unsaturated monomer, based on a solids weight of the at least two polyphenolic compounds.

12. The binder composition of claim 1, wherein the unsaturated monomer is nonionic, and wherein the binder composition comprises less than 3 wt % of ionic monomers.

13. The binder composition of claim 1, further comprising a copolymer of one or more vinyl aromatics and at least one of maleic anhydride and maleic acid; an adduct or polymer of styrene, at least one of maleic anhydride and maleic acid, and at least one of an acrylic acid and an acrylate; or a mixture thereof.

14. A binder composition, comprising a reaction product of an unsaturated monomer and at least two polyphenolic compounds, wherein:

the at least two polyphenolic compounds are selected from the group consisting of: a tannin, a lignin, a novolac resin, a modified phenol formaldehyde resin, bis-phenol A, and humic acid, and the unsaturated monomer is selected from the group consisting of: an unsaturated glycidyl ether, an unsaturated glycidyl ester, an unsaturated mono-epoxide, an unsaturated methylol compound, maleic anhydride, and any mixture thereof, wherein the binder composition comprises about 0.05 wt % to 10 wt % of the unsaturated monomer, based on a solids weight of the at least two polyphenolic compounds.

15. The binder composition of claim 14, further comprising water, wherein the binder composition comprises about 1 wt % to about 80 wt % of the water, based on a solids weight of the at least two polyphenolic compounds.

16. The binder composition of claim 14, wherein the unsaturated monomer comprises at least two compounds selected from the group consisting of: an unsaturated glycidyl ether, an unsaturated glycidyl ester, an unsaturated mono-epoxide, an unsaturated methylol compound, and maleic anhydride.

17. The binder composition of claim 14, and wherein the binder composition comprises less than 3 wt % of ionic monomers.

18. The binder composition of claim 14, wherein the at least two polyphenolic compounds are selected from the group consisting of: a tannin, a lignin, a novolac resin, bis-phenol A, and humic acid.

19. A composite product, comprising:
a plurality of lignocellulose substrates and an at least partially cured binder composition, wherein the binder composition, prior to curing, comprises:
a reaction product of an unsaturated monomer and at least two polyphenolic compounds, wherein:
the at least two polyphenolic compounds are selected from the group consisting of: a tannin, a lignin, a novolac resin, a modified phenol formaldehyde resin, bis-phenol A, and humic acid, and
the binder composition comprises about 0.05 wt % to 10 wt % of the unsaturated monomer, based on a solids weight of the at least two polyphenolic compounds.

20. The composite product of claim 19, wherein the unsaturated monomer is selected from the group consisting of: an unsaturated glycidyl ether, an unsaturated glycidyl ester, an unsaturated mono-epoxide, an unsaturated methylol compound, maleic anhydride, and any mixture thereof.

* * * * *